United States Patent [19]

Rapoport et al.

[11] Patent Number: 5,732,696
[45] Date of Patent: Mar. 31, 1998

[54] POLYSOMNOGRAPH SCORING

[75] Inventors: David M. Rapoport, New York; Robert G. Norman, Deer Park, both of N.Y.

[73] Assignee: New York University, New York, N.Y.

[21] Appl. No.: 271,212

[22] Filed: Jul. 5, 1994

Related U.S. Application Data

[63] Continuation of Ser. No. 852,555, Mar. 17, 1992, abandoned.

[51] Int. Cl.$^6$ .............................. A61B 5/00; A61B 5/04
[52] U.S. Cl. ............................. 128/630; 128/731
[58] Field of Search ..................... 128/630, 731, 128/733; 395/900, 924; 364/413.02, 413.04

[56] References Cited

U.S. PATENT DOCUMENTS

| | | | |
|---|---|---|---|
| 3,774,593 | 11/1973 | Hakata et al. | 128/2.1 B |
| 4,550,736 | 11/1985 | Broughton et al. | 128/731 |
| 4,585,011 | 4/1986 | Broughton et al. | 128/733 |
| 4,776,345 | 10/1988 | Cohen et al. | 128/731 |
| 5,047,930 | 9/1991 | Martens et al. | 364/413.04 |
| 5,299,118 | 3/1994 | Martens et al. | 128/731 X |

OTHER PUBLICATIONS

Anch AM, Browman CP, Mitler MM, Walsh JK. Sleep: A Scientific Perspective. Prentice Hall, Englewood Cliffs, 1988.

Rechtschaffen, A. and Kales, A. A manual of standardized terminology, techniques and scoring system for sleep stages of human subjects. NIH publication #204, 1968.

Hauri, P. The Sleep Disorders (2nd Ed.), Scope (Uphohn), Kalamazoo, MI. 1982.

Roffwarg, H.A. ASDA Position statement on automatic scoring. Sleep 13(3):284–85, 1990.

Phillipson, E.A. et al. Indications and standards for cardiopulmonary sleep studies. ATS consensus conference report. Am Rev Resp Dis 139:559–68, 1989.

Kubicki, St, Holler, L, Berg, I, Pastelak–Price, C and Dorow R. Sleep EEG evaluation: A comparison of results obtained by visual scoring and automatic analysis wih the Oxford sleep stager. Sleep 12(2):140–149, 1989.

Palm,L, Elmqvist,D, and Blennow,G. Automatic versus visual EEG sleep staging in preadolescent children. Sleep 12(2):150–156, 1989.

Ferri, R, Ferri,P, Colognola,MA et al. Comparison between the results of an automatic and a visual scoring of sleep EEG recordings. Sleep 12(4):354–362, 1989.

Smith JR. Computers in sleep research. CRC. Crit. Rev. Bioeng. 3(2):93–148, 1978.

Hasan J. Automatic analysis of sleep recordings: A critical review. Annals of Clinical Research 17:280–287, 1985.

Demermuth G. Electronic data processing in pediatric EEG research. Neuropadiatrie 4:349–74, 1971.

Hoffmann R, Moffitt A, Wells R, Sussman P, Pigeau R, Shearer J. Quantitative description of sleep stage electrophysiology using digital period analytic techniques. Sleep 7(4):356–364, 1984.

(List continued on next page.)

*Primary Examiner*—Jennifer Bahr
*Assistant Examiner*—Samuel Gilbert
*Attorney, Agent, or Firm*—Darby & Darby

[57] ABSTRACT

A method and apparatus for scoring EEG, EMG and EOG data, for sleep stages, in order to simulate the scoring results achieved by human scorers in which a general determination is initially made of the presence or absence of a plurality of elemental events. This determination is employed to develop the probabilities of the occurrence of the elemental events. These probabilities are then employed as a base to determine the probabilities of the occurrence of Rechtschaffen and Kales events. The Rechtschaffen and Kales event probabilities may be modified to account for the stage 2 rule and the REM rule. These Rechtschaffen and Kales event probabilities are then employed to determine the probability distribution of possible sleep stages for each epoch of the polysomnograph and choose the most likely score.

7 Claims, 24 Drawing Sheets

OTHER PUBLICATIONS

Kuwahara H, Higashi H, Mizuki Y, Matsunari S, Tanaka M, Inanaga K. Automatic real–time analysis of human sleep stages by an interval histogram method. Electroenceph. Clin. Neurophysiol. 70(3):220–9, 1988.

Kayed K, Roberts S, Davies WL. Computer detection and anlysis of periodic movements in sleep. Sleep 13(3):253–261, 1990.

Kemp B. An optimal monitor of the rapid–eye–movement brain stage. Biol. Cybern. 54:133–139, 1986.

Ktonas PY, Smith JR. Automatic REM detection: Modifications of an existing system and preliminary normative data. Int J BioMed Comput. 9:109–124, 1978.

Mercia, H. and Gaillard, J.M. Internal structure of sleep cycles in a healthy population. Sleep 9(4):502–512, 1986.

Mercia, H and Gaillard, JM. Statistical description and evaluation of the interrelationships of standard sleep variables for normal subjects. Sleep. 8(3):261–273, 1985.

Martin WB, Johnson LC, Viglione SS, Naitoh P, Joseph R, Moses Jo. Pattern recognition of EEG/EOG as a technique for all night sleep state–scoring. Electroenceph. Clin. Neurophys. 32:417–427, 1972.

Ray SR, Lee WD, Morgan CD, Airth–Kindree, W. Computer sleep stage scoring–An expert system approach. Int. J. Biomed. Comp. 19:43–61, 1986.

Stanus E, La croix M, Kerkhofs M and Mendlesicz J., Automated Sleep Scoring: a comparative reliability study of two algorithms. Electroenceph. Clin. Neurophys. 66:448–456, 1987.

A. Kumar, A Real–Time System for Pattern Recognition of Human Sleep Stages By Fuzzy System Analysis. Pattern Recognition, vol. 9, pp. 43–46, 1977.

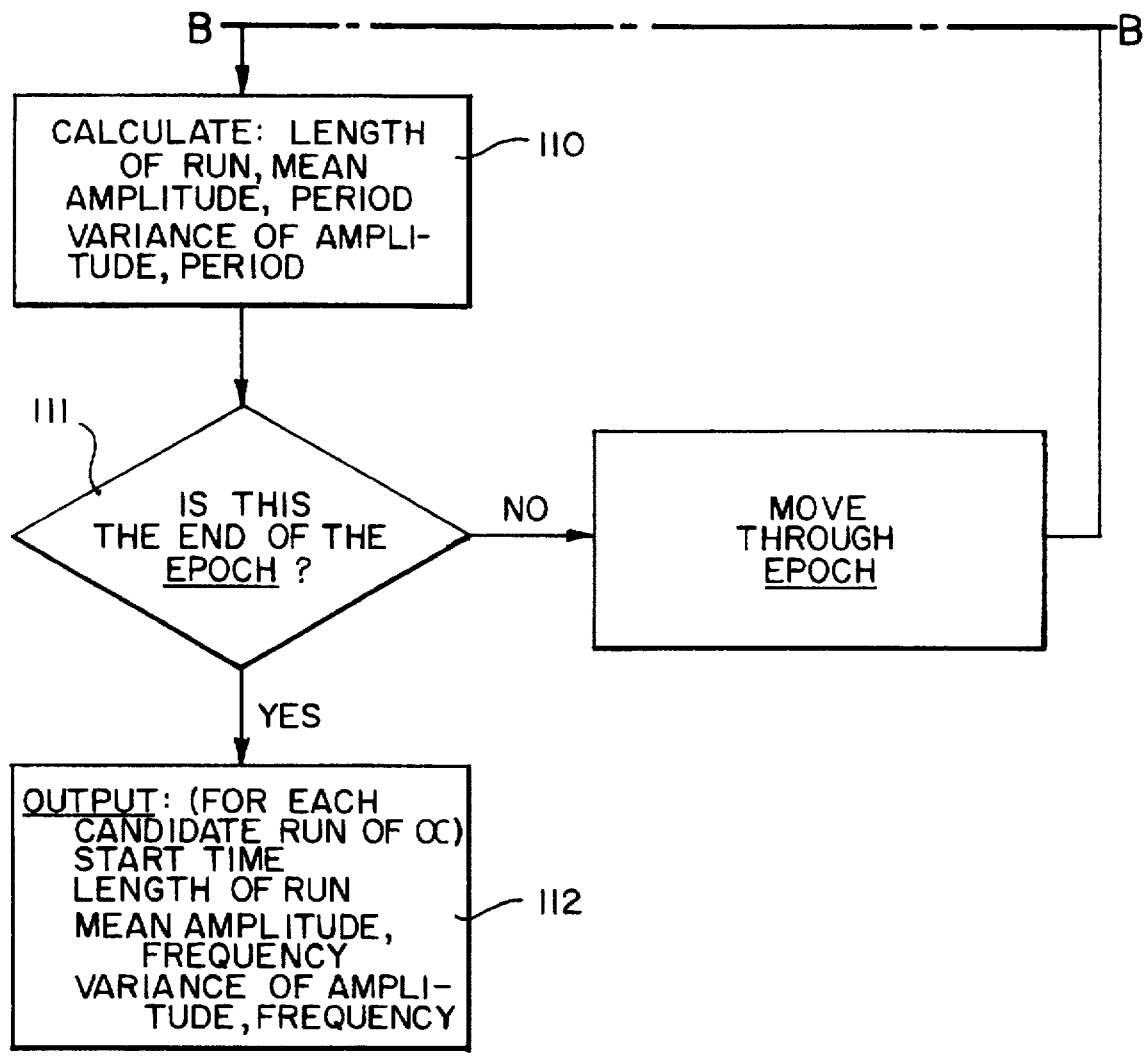

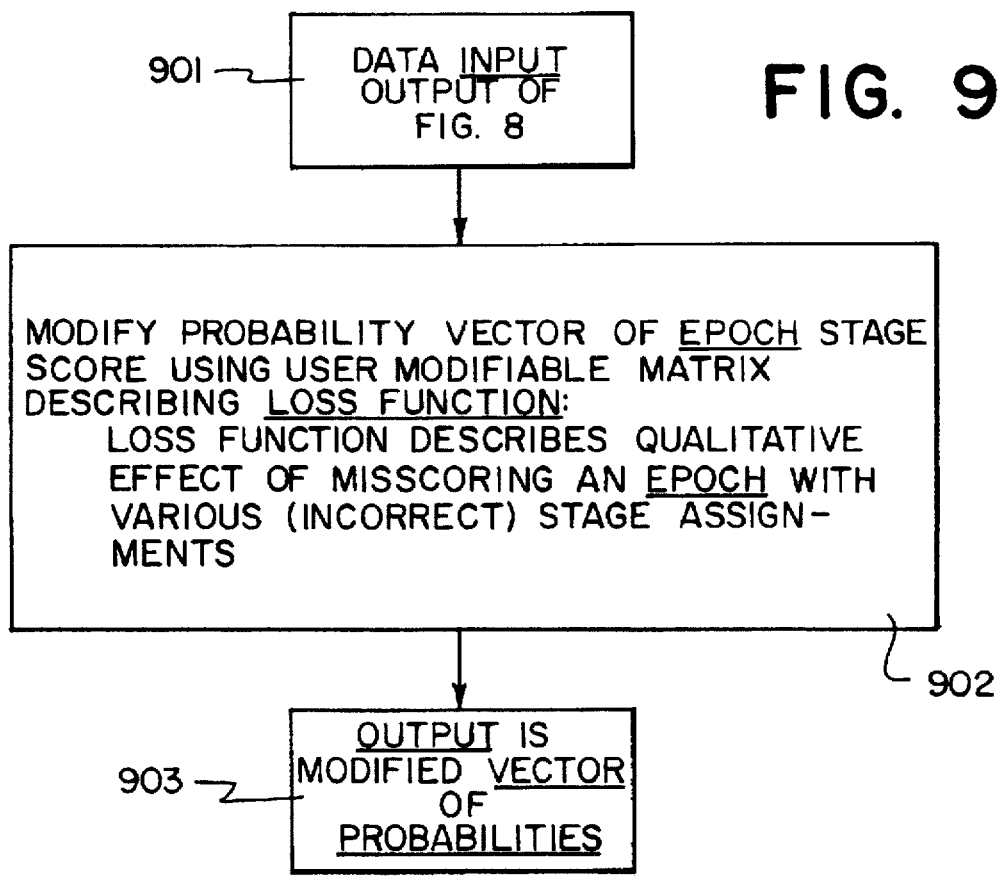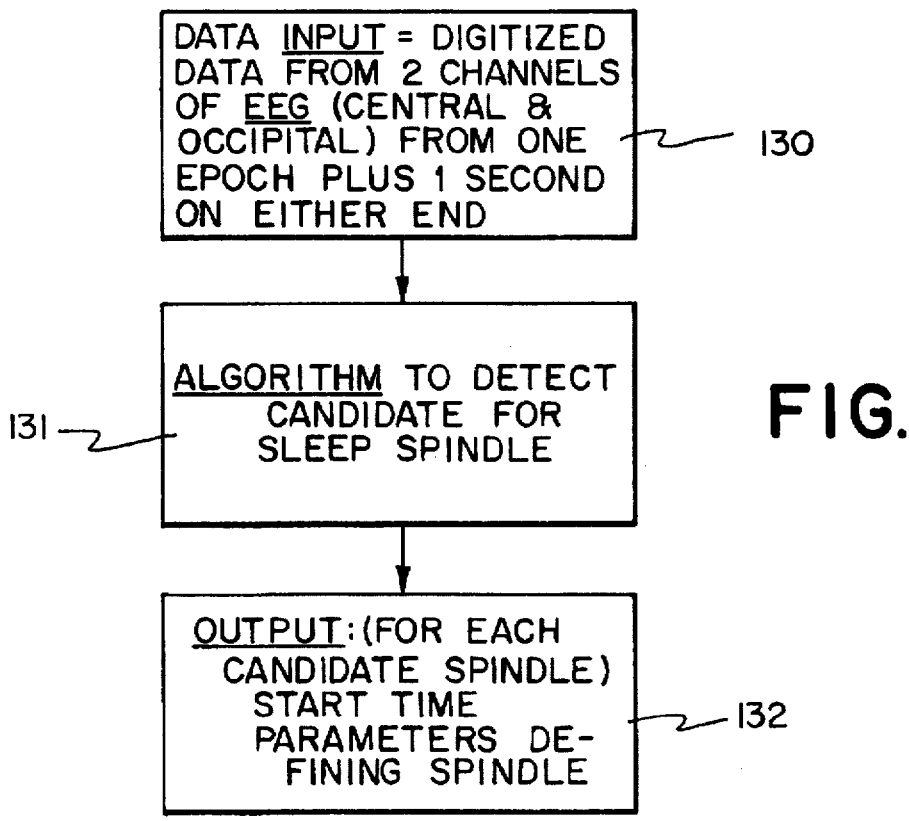

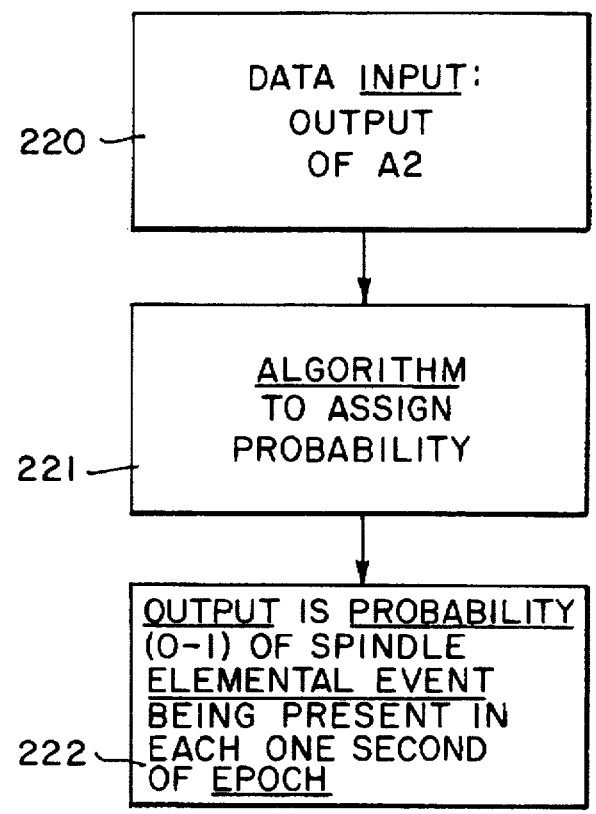

POLYSOMNOGRAPH SCORING

This application is a continuation, of application Ser. No. 07/852.555, filed Mar. 17, 1992, now abandoned.

FIELD OF THE INVENTION

This invention relates to a method and apparatus for scoring polysomnographs to ascertain the sleep stages of epochs of data obtained from EEG, EMG and EOG signals.

BACKGROUND OF THE INVENTION

The references discussed in the following discussion of the background of the invention are identified in greater detail in the list of references at the end of this specification.

Standard practice in clinical and research sleep laboratories entails the collection of electrophysiological signals from sleeping patients and animals. These signals include electroencephalogram (EEG) signals, electrooculogram (EOG) signals and electromyogram (EMG) signals obtained typically of the chin. These signals are recorded on paper or electronic media and analyzed in "epochs" defined as discrete periods of time, typically 20 or 30 seconds long. All the signals are examined in such an epoch by a trained technician. Conventionally a standardized set of rules defined by Rechtschaffen and Kales is used by the scorer to assign one of several unique scores or sleep stages to the epoch. These stages include Awake, Non-REM stages 1, 2, 3, 4, REM, movement time and a variety of special stages. Although the Rechtschaffen and Kales rules are well defined and have been fully standardized, typical sleep records frequently show conflicting trends in the signals and may satisfy more than one rule simultaneously, among which the scorer must choose by subjective criteria. In addition, one or more signals may be weak, atypical, or confounded by artifacts in a given individual, resulting in decisions about the inputs to applying a rule which are based on the likelihood that certain events are actually present. Human scorers have the ability to reconcile these differing inputs with the rigid rules of Rechtschaffen and Kales and come up with the most reasonable choice of the most likely score. In general two well trained human scorers agree in the choice of a score to assign to each segment or epoch of a record of sleep data in about 80–90% of cases.

Computer programs have been developed in an attempt to duplicate this human ability to implement the Rechtschaffen and Kales rules. This is especially attractive as more and more sleep laboratories have moved to collecting the raw electrophysiological data on electronically legible media (CNS and Nicolet and Sensormedics). Computerized scoring of this data has enormous potential applicability since a well-trained technologist can take 2–8 hours to score a typical single night of data by hand.

Currently, there are several commercial computer systems designed to record an entire night of data in digital format. Although these systems do a good job of collecting the waveforms and detecting movement, respiratory and cardiac abnormalities, their algorithms for scoring the sleep are still primitive as compared with the scores obtained by a technologist, even in normal subjects (Kubicki, Palm, Ferri, Smith). In patients with severe sleep abnormalities such as those typically investigated in the sleep laboratory, performance of these computerized scoring systems has been unsatisfactory in that they systematically disagree with experienced human scorers. In keeping with this, the present official position of professional organizations such as the American Sleep Disorders Association (Roffwarg) and the American Thoracic Society (Phillipson) is that available computerized systems for scoring of sleep records are not acceptable.

Past investigations into computerization of sleep scoring have concentrated on algorithms that rigidly implement Rechtschaffen and Kales rules using a flow chart or decision tree approach, each step of which is a "yes or no" decision. These algorithms focus on identifying individual waveforms which are characteristic of each stage of sleep (elemental events). The Rechtschaffen and Kales rules specify that a sleep stage is assigned in a categorical manner based on the presence or absence of these elemental events. This approach leaves little room for ambiguity as to whether an elemental event has been correctly identified, nor does it allow for conflicting information (e.g., elemental events may be present which suggest more than one stage). A human scorer confronted with these situations will make a rational decision based on experience as to which stage is most likely (Hasen). This option has not been incorporated into any existing computer algorithms which uses a deterministic approach. The incorporation of uncertainty is the basis of the present approach.

Programs to identify elemental events have been developed which work relatively well on records having classical waveform morphology. These have used techniques including Fourier analysis (Dermuth), period amplitude analysis (Hoffmann), interval histogram analysis (Kuwahara), and other (Kumar, Sherif, Ktonas, Kayed, Kemp). However, these programs do not succeed in using this preliminary analysis to assign sleep stage which consistently agree with human scoring (Kubicki, Palm, Ferri, Smith, Hasan). Additional problems occur when these algorithms are used on records where waveform morphology is less than classical (which is often the case in clinical settings). A few attempts have been made to incorporate ambiguity into the decision making process. These have relied on classical statistical techniques (e.g., discriminant analysis) (Smith) or on pattern analysis (Martin, Kumar). Recently an attempt to use an expert system approach (Ray) was published, but this relied on characterization of "patient types" and resulted in a long learning process for the algorithm which needs to be repeated for each patient to be evaluated. Only one author has evaluated the use of Decision Theory in sleep scoring (Stanus), but this was not used in the context of the standard Rechtschaffen and Kales scoring system.

SUMMARY OF THE INVENTION

Briefly stated, in accordance with the invention, a method and apparatus are provided for scoring polysomnograph signals. Known polysomnograph signals, such as EEG signals, EMG signals and EOG signals are separated into a plurality of sequential epochs. Employing these input signals, a means and method are provided for determining whether or not there is a possibility of the existence of each of a plurality of elemental events in the signals of each of said epochs. Such elemental events may include alpha waves, delta waves, k complex waves, spindles, etc. The elemental events which have been determined to be possibly present may be considered to constitute candidates. The probability of each of the occurrences of each of these candidates in each epoch is then determined. The probabilities of occurrence of events relevant to conventional R&K sleep stage assignment (R&K events) are then determined from the probabilities of occurrence of the elemental events. From these R&K event probabilities the likelihood of each possible stage of sleep being present is calculated (e.g. a probability distribution of sleep stage is calculated for each epoch).

The probability distribution of sleep stages can be modified to account for stage 2 rules, REM rules, loss factors and prior probability functions.

BRIEF DESCRIPTION OF THE DRAWINGS

In order that the invention may be more readily understood, it will now be disclosed in greater detail with reference to the accompanying drawings, wherein:

FIGS. 3A, 3B and 3C together constitute a flow diagram of a routine for detecting alpha waves;

FIG. 9 is a flow diagram of a routine for applying a loss function;

FIG. 11 is a flow diagram of a routine for detection of sleep spindle events;

FIG. 16 is a flow diagram of a routine for assigning the probability of a sleep spindle event;

FIG. 17 is a flow diagram of a routine for assigning the probability of a delta event;

DEFINITIONS

Figure 1:
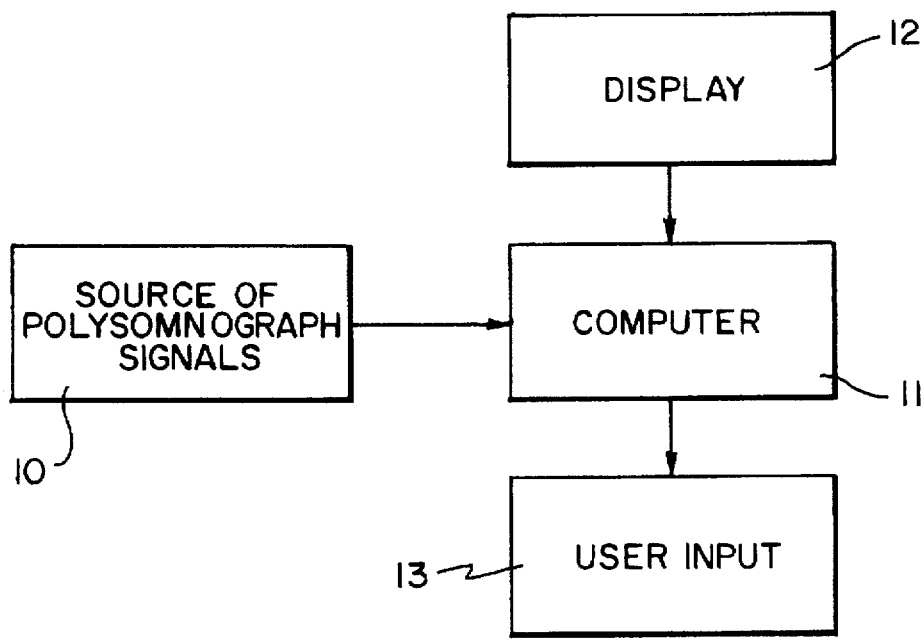
FIG. 1 is a block diagram of a system that may be employed in the invention.

Before proceeding with a detailed discussion of the invention, it is necessary to provide a definition of terms that will be employed herein, as follows:

1. ELEMENTAL EVENT: An individual waveform or complex on a single channel (or multiple channels) of data which is recognizable to the human eye, and which is used in applying the standardized sleep scoring rules.

ELEMENTAL EVENTS discussed in the present application include:

A1: run of alpha ($\alpha$) waves
A2: sleep spindle
A3: delta ($\delta$) wave
A4: k complex
A5: low EMG
A6: very low EMG
A7: high EMG
A8: transient increase in EMG
A9: in-phase eye movement
A10: out-of-phase eye movement
A11: slow rolling eye movement These ELEMENTAL EVENTS are defined as being present with a unique PROBABILITY (see 2). They are assigned as being present/absent in a single 1 second portion of the physiological record.

The invention, however, is not limited to these specific ELEMENTAL EVENTS.

2. PROBABILITY of an ELEMENTAL EVENT: the likelihood (with a value from 0 to one), calculated from multiple factors, that a detected event (candidate) is in fact what it was labeled. Each ELEMENTAL EVENT has a unique probability of being present. However, any given waveform can have several probabilities of being different ELEMENTAL EVENTS.

3. Rechtschaffen and Kales EVENT: A waveform, or complex of ELEMENTAL EVENTS, which is used by the Rechtschaffen and Kales rule system to provide important input into the decision to label an epoch (segment) of a sleep record as belonging to one of the standard sleep stages (NREM 1, NREM 2, NREM 3, NREM 4, REM, AWAKE, MOVEMENT TIME, etc)

Presently identified Rechtschaffen and Kales EVENTS include:

C1: alpha ($\alpha$) waves in <25% of epoch
C2: alpha waves in 25-50% of epoch
C3: alpha waves in >50% of epoch
C4: single sleep spindle in epoch
C5: multiple sleep spindles in epoch
C6: delta ($\delta$) waves in <20% of epoch
C7: delta waves in 20-50% of epoch
C8: delta waves in >50% of epoch
C9: k complexes in epoch
C10: low EMG for most of epoch
C11: very low EMG for most of epoch
C12: high EMG for most of epoch
C13: transient increase in EMG during epoch
C14: in-phase eye movements
C15: out-of-phase eye movements (REMs)
C16: slow rolling eye movements
C17: 5 second arousal
C18: significant artifacts It is of course apparent that the invention is not limited to these specific events, and may vary in accordance with future variations of the Rechtschaffen and Kales events, if such variations occur, for application of other standardized rules for scoring sleep.

4. PROBABILITY of an Rechtschaffen and Kales EVENT: the likelihood (with a value from 0 to one), calculated from multiple factors, that a detected Rechtschaffen and Kales EVENT (candidate) is in fact what it was labeled.

5. EPOCH: a discrete period of time in the continuous physiological record, typically 30 seconds of data. By convention, Rechtschaffen and Kales rules assign a single sleep stage score to each epoch.

6. SLEEP STAGE: a single stage of sleep defined by multiple physiological parameters outlined in the Rechtschaffen and Kales Scoring Manual and assigned to each EPOCH of a sleep record.

Presently scores possible include:

Non-REM (NREM) Stage 1

Non-REM (NREM) Stage 2

Non-REM (NREM) Stage 3

Non-REM (NREM) Stage 4

Rapid Eye Movement (REM) Stage

Awake

Movement Time

Artifact

7. PRIOR probability function: A function which modifies the probability of each Rechtschaffen and Kales Stage assigned to each EPOCH (see 6) based on information not contained in that epoch. Examples of this include the expected normal distribution of time spent in each stage for a night in normal and abnormal subjects the expectation of transition from one stage to another (Markov transition matrix)

the duration of continuous time spent in a stage before transition occurs to another stage (Frequency analysis of consecutive epochs)

8. LOSS FUNCTION: A function which assigns a numerical value (loss) to each possible erroneous assignment of a sleep stage to an epoch. The magnitude of the loss reflects the severity of the error and allows negative impact of a choice between STAGE assignments to be minimized.

One implementation of a loss function is derived from the subjective assessment given by experienced sleep scorers who were asked to rate the severity of the consequences of all possible scoring errors.

DETAILED DESCRIPTION OF THE INVENTION

As illustrated in FIG. 1, the invention may employ a conventional computer system, such as an IBM compatible microcomputer. A source of signals 10 includes a convention source of EEG, EMG and EOG signals. The signals may be applied to the computer 11 in conventional manner. The computer is provided with a program for processing these signals, in a manner that will now be discussed, as well as a conventional display 12 and user input device 13 such as a keyboard 13.

Figure 2:
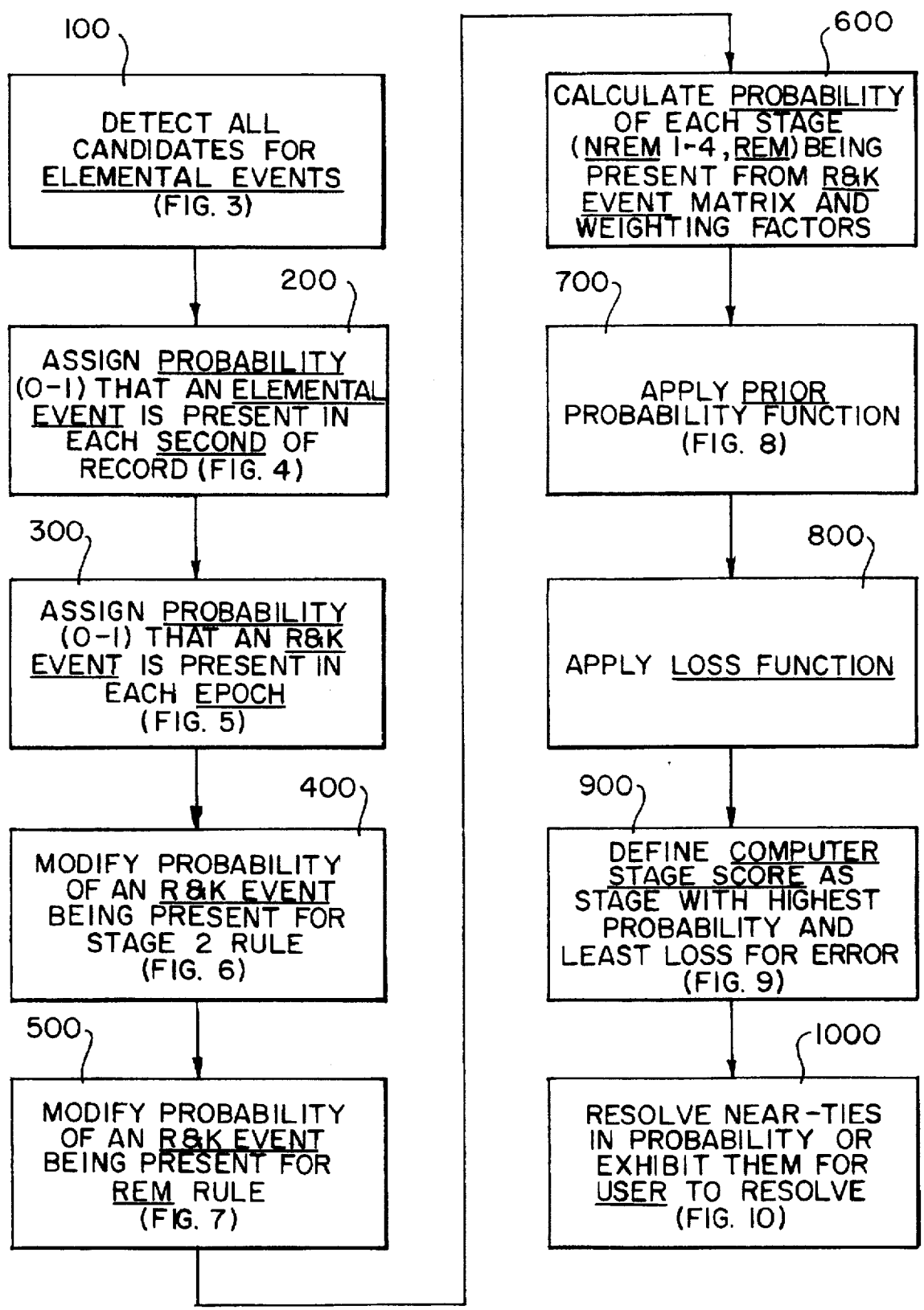
FIG. 2 is an overall flow diagram of the method of the invention.

FIG. 2 is an overall flow chart for a polysomnograph scoring program in accordance with the invention. In the first step 100, the input signals are analyzed to detect all candidates for the Elemental Events. In this routine, each of the epochs is analyzed to determine if any signals therein indicate the possibility of the existence of any of the Elemental Events. The test outputs a list of candidates of the Elemental Events for further analysis.

Figure 3A:
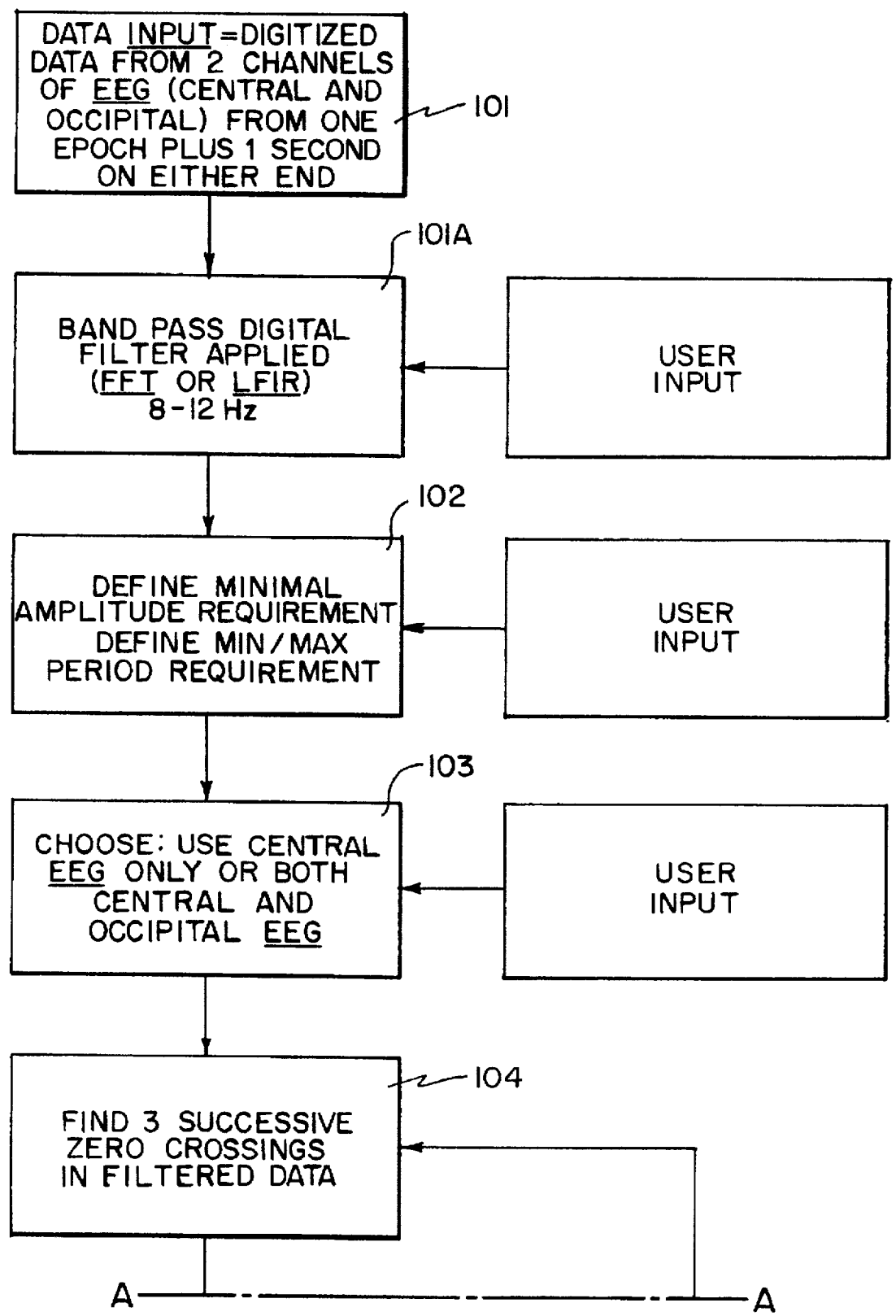
Figure 3B:
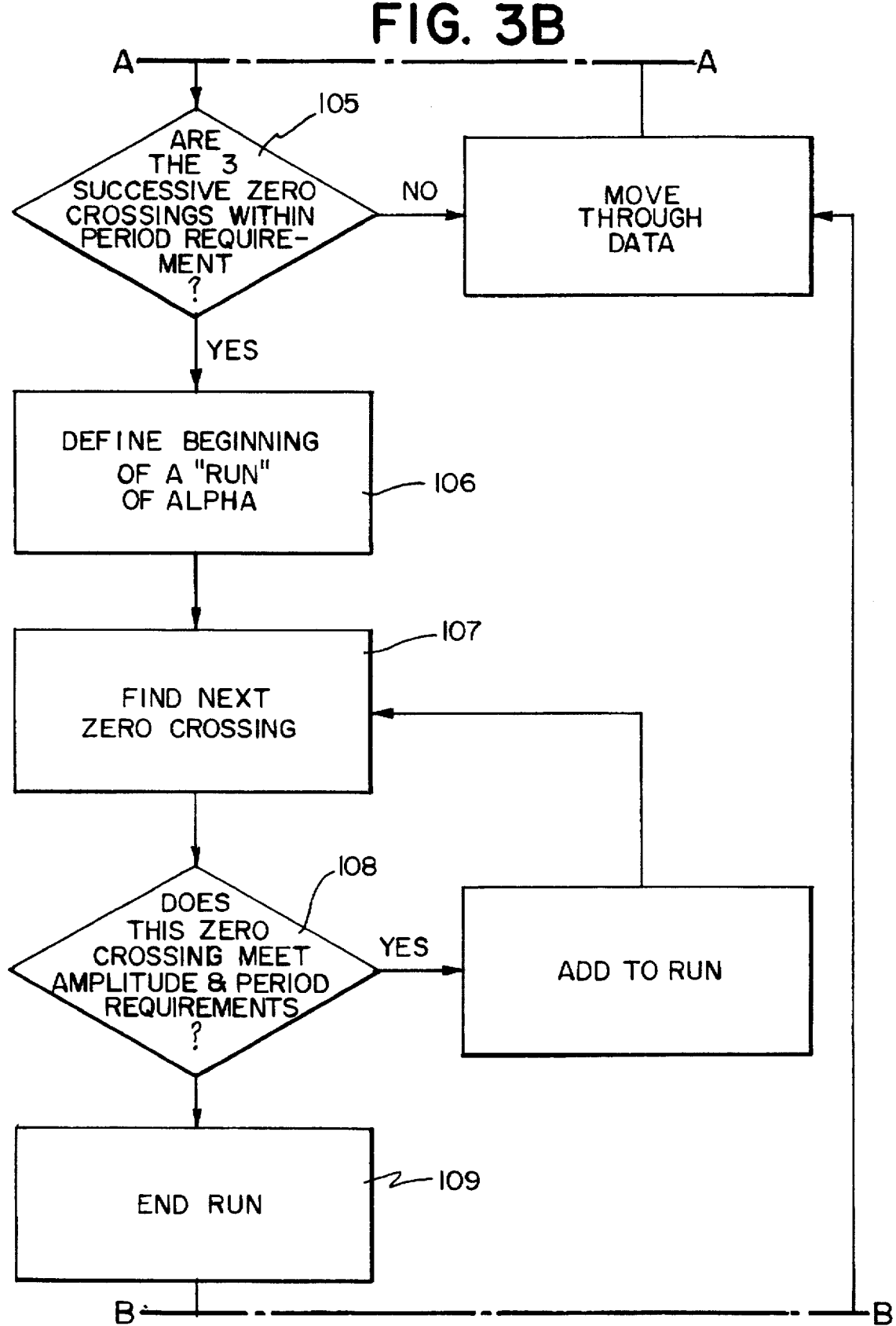

One example of a routine in accordance with the invention for detecting the possibility of the existence of an alpha wave in an epoch is shown in FIGS. 3A and 3B. In this routine, at step 101 the conventional digitized data is input, for example from the central and occipital channels of EEG, for one epoch, as well as for one second before and one second after the current epoch. These signals are applied to a band pass filter at step 101A, to remove frequencies that are not applicable to alpha waves. This step may interact with user input, as illustrated, to control the range of frequencies of the band pass filter. In the next step 102, specifications are determined for minimum amplitude, as well as the maximum and minimum periods that will be considered to constitute a valid element. These parameters of these functions may also be controlled by user input, as illustrated. In the next step 103, the user may select whether it is desired to employ only the central EEG signals, or whether the test should also include the occipital signals. The thus processed signals are now tested for the presence of three successive zero crossings, at step 104, and at step 105 it is determined whether these zero crossings are within the period requirements set in block 102. If the zero crossings are within this requirement, the start of the run of zero crossings is defined at block 106. Otherwise the testing of further signals in the epoch is continued by returning to block 104.

Referring now to FIG. 3B, the signals are now tested at block 107 to find the next zero crossing. If the detected zero crossing is still within the period requirement, as tested at block 108, it is added to the run of zero crossings, and the program jumps back to step 107 to detect further zero crossings. If the last found zero crossing does not meet these requirements, the run is stopped at block 109, and its length, mean amplitude, period, and variance of amplitude are calculated at block 110. If the full epoch has not been tested, the program branches back at block 111 to continue the testing at block 104. Otherwise, the calculated data are output at block 112.

Routines of this type are also provided for each of the other Elemental Events, based upon the known characteristics and parameters of the other Elemental Events.

The analysis of block 100 only selects candidates for Elemental Events. The tests made in this portion of the program essentially analyze only the data of the current epoch, and do not consider data from other epochs. Since the existence of an Elemental Event may be dependent upon the conditions, for example, in adjacent epochs, more detailed analysis may eventually determine that candidates found in the program of block 100 should not be considered as being present. While such an eventuality may not be significant with respect to the testing for the presence of alpha waves, it can be in a test for other events such as eye movement.

Referring again to FIG. 2, the output of the routines of block 100 are now processed, in block 200, to assign a probability that each Elemental Event is present in each epoch. As defined above, the probability of an Elemental Event is the likelihood (having a value from 0 to 1, i.e. not just a yes or no result) that the detected candidates of the Elemental Events are actually present. The tests of the probabilities are also effected for each second of each epoch.

Figure 4A:
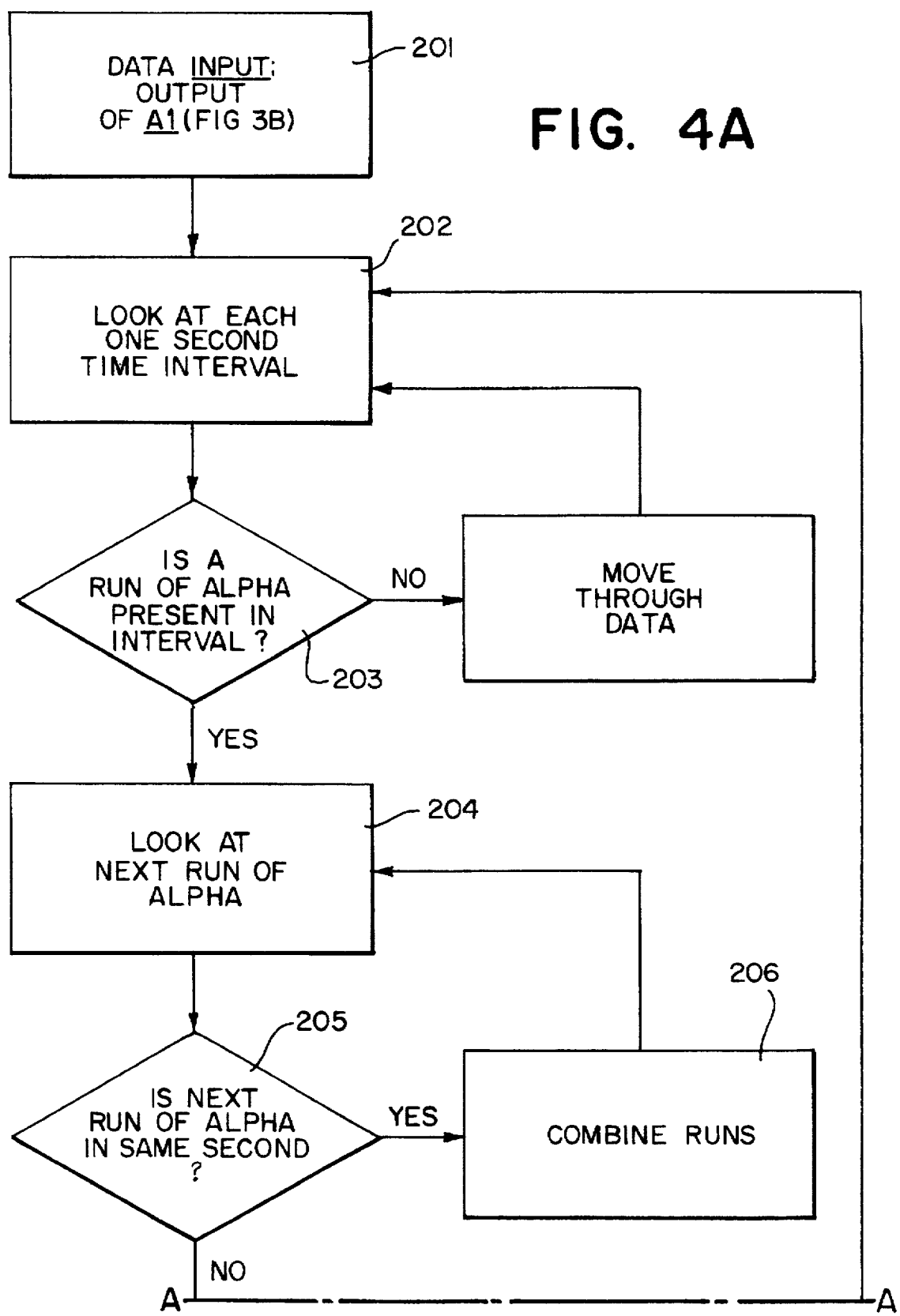
FIGS. 4A, 4B together constitute a flow diagram of a routine for assigning the probability of the presence of alpha waves.
Figure 4B:
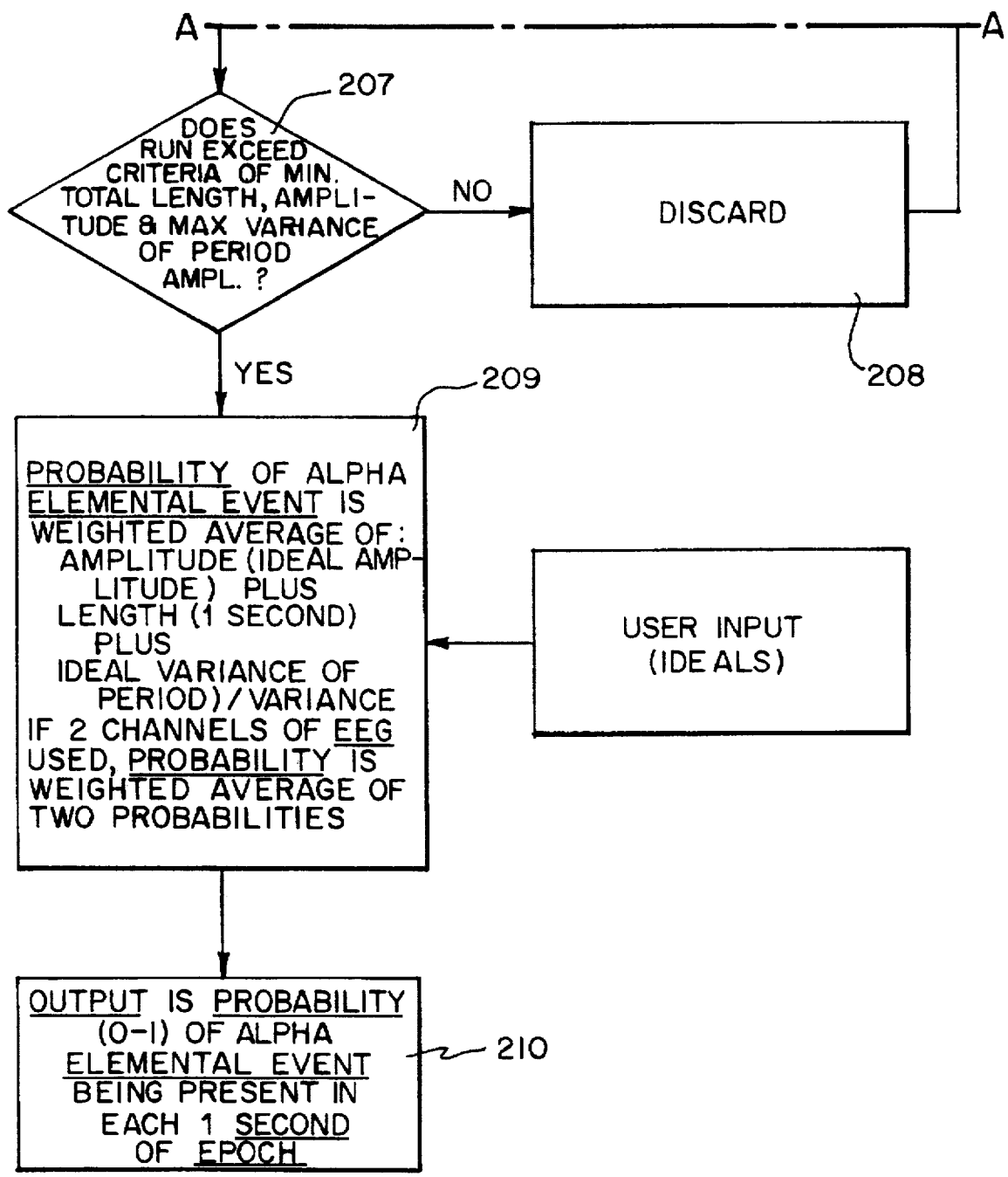

An example of the routine of block 200, for alpha waves, is illustrated in FIGS. 4A and 4B. As illustrated, the results of the routine of FIG. 3B are input, at block 201, and each second of the current epoch is analyzed at block 202. In block 203 it is determined, on the basis of the output of the routine of FIG. 3B, whether or not a candidate run of alpha waves has been indicated to be present. If no such run is indicated to be present, the program branches back to block 202 to analyze the next second. If it has been indicated by the routing of FIG. 3B that a run of alpha is present in the present second, then the program looks at the next run in step 204, and determines, at block 205, if the next run of alpha waves is in the same second. If it is, the runs are combined, at block 206, and the program branches back to block 204.

If the next run of alpha is not during the second currently being analyzed, a test is made at block 207 to determine if the run exceeds a given criteria with respect to minimum total length, minimum amplitude, and maximum variance of the period. These criteria are selected empirically by comparison of the results of the overall program with the results of human scorers, to achieve the best match between the results of the program and the results of human scorers.

In this regard, it is noted that the program and algorithms of the present invention are intended primarily to achieve the same results as human scorers, and not necessarily to achieve results that are "absolutely" correct.

If the run does not exceed the minimum criteria, it is discarded, at block 208, and the program branches back to continue analyzing each further second of the epoch. If, however, the minimum criteria has been exceeded, the program then calculates the weighted average of the amplitude, length and variance, at block 209, to provide an output probability, from 0 to 1, from block 210. The parameters of the weighted average may be adjusted by user input, as above discussed, to provide the best match between the computer results and the results of human scorers. As discussed above, the testing of FIGS. 4A and 4B is effected for each second of each epoch.

The Rechtschaffen and Kales scoring rules aren't based directly on the eleven Elemental Elements discussed above. For instance, the Elemental Events include all delta activity, but the Rechtschaffen and Kales rules specify the required amount of Delta activity in epoch, i.e. whether it is less than 20% of the epoch, etc. The 18 Rechtschaffen and Kales events are basically the events that are used for the scoring purposes, in accordance with the invention, but in order to determine the probability of these 18 events, it is necessary, in accordance with the invention, to make preliminary probability assignments.

The probabilities determined of the existence of each Elemental Event in each epoch, at block 200 of FIG. 2, are now employed to assign a probability, in block 300, that an Rechtschaffen and Kales event is present. In this part of the method, the outputs of the 11 routines assigning probabilities of the existence of the Elemental Events, for each second of each epoch, are combined in a probabilistic manner.

For example, if there are a number of assignments of probability of delta for each second, then these assignment may be added together to determine if they meet the Rechtschaffen and Kales requirement of 50% of the epoch. The Rechtschaffen and Kales rules require consideration of events occurring in epochs other than the epoch being currently considered. Basically, a first estimate of the sleep stage is made on the basis of only the currently considered epoch. The information concerning the current epoch is processed by applying a weighting matrix to convert the vector of Rechtschaffen and Kales event probabilities to a vector describing a probability distribution of sleep stages for that epoch.

Figure 5A:
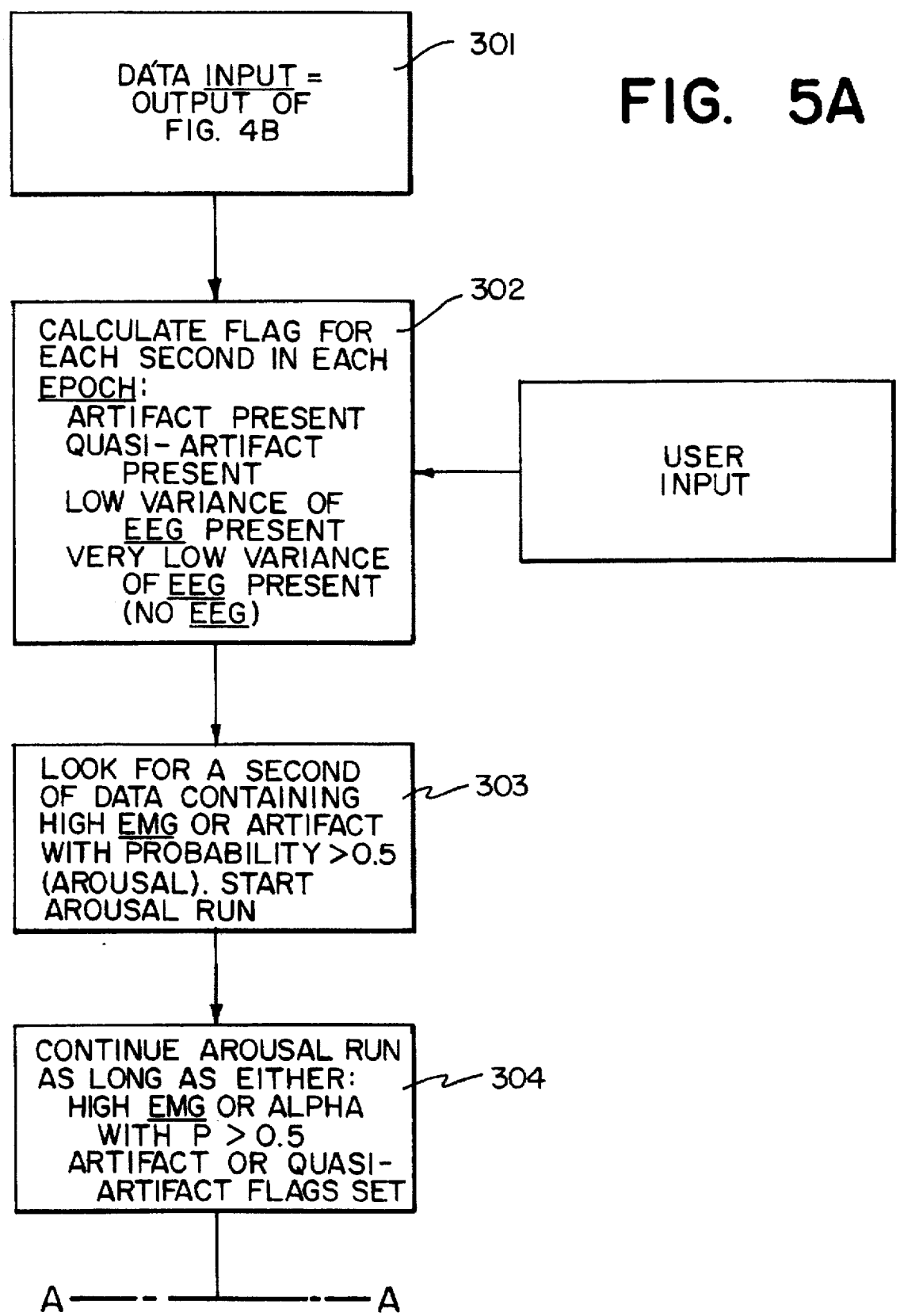
FIGS. 5A, 5B, 5C and 5D together constitute a flow diagram of a routine for assigning the presence of Rechtschaffen and Kales events.
Figure 5B:
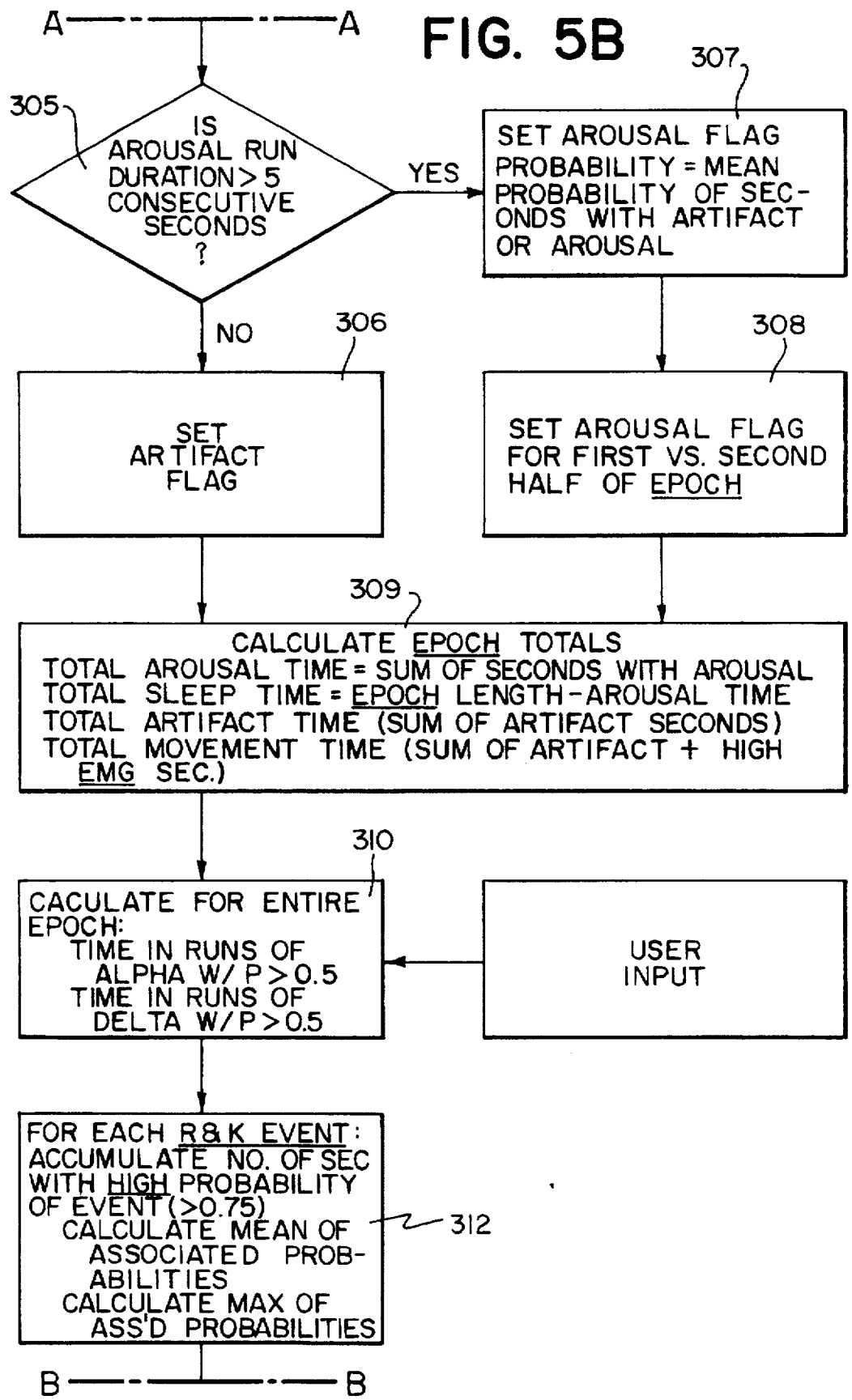

Furthermore, certain modifications are applied to this distribution. For example, if consideration of only the current epoch suggests the presence of Stage 2, except for the fact that it doesn't have a spindle or a k complex event which are required for stage 2, then Stage 2 may in fact be considered to be present if the current epoch is bracketed, within three minutes, of these events in other epochs. In addition, since eye movements do not occur all of the time, it is necessary to look forward and backward in time for the occurrence of eye movement, e.g. in assigning a probability for REM sleep, if other criteria indicate the possibility of the existence of REM sleep An example of a routine for assigning presence of Rechtschaffen and Kales events is illustrated in FIGS. 5A, B and C. In this routine, the probabilities assigned by the routine of FIGS. 4A and 4B is input at block 301. The first phase of the routine determines whether or not each second contains valid data. At block 302, artifacts are detected, as well as quasi artifacts (high frequency noise), the presence of low variance of EEG, and the presence of very low variance of EEG (no EEG). Flags are set for these conditions. The existence of very low variance of the EEG might indicate that this data might be invalid. For example the patient may have been disconnected from the measuring equipment. As shown in the illustration, user input may be employed to vary the conditions required for the setting of the flags. These flags are then used to further modify probability assignments.

As shown at block 303, on the basis of the information determined in block 302, and the setting of the various flags, a determination is made of the occurrence of an arousal. An arousal occurs, for example, when the patient wakes up for a brief period of time. Such arousals affect the Rechtschaffen and Kales rules.

To find arousals, the program looks for an epoch that has an increase in EMG where the patient started moving. This is the prime indicator of an arousal. The program then tries to find a 5 second period, such a period indicating the present of an arousal. This is a combination of whether or not alpha activity is present, whether or not artifact activity is present, and whether or not high EMG is present. Any one of those three, once an arousal has been started, will effect its continuance.

The routine for detection of arousals continues at block 304. If the arousal has lasted for more than 5 seconds, as detected at block 305, an arousal flag is set at block 307. Otherwise, at block 306, an artifact flag is set. In block 308, the arousal flag is set to indicate whether the arousal has occurred in the first half or the second half of the current epoch. This flag is used to determine whether stage 2 or REM defining events occuring in the second half of an epoch should be used to implement a placement criteria. This flag is used in combination with probability assignments of previous epoch events to make this determination.

As shown at block 309, the program now calculates the epoch totals, such as the total arousal time, the total sleep time, the total artifact time and the total movement time.

The program now determines the times in runs of alpha and delta, at block 310, and the program branches back to continue the same routine for each second of the epoch.

At block 312, the mean of associated probabilities, and the maximum of the associated probabilities, is calculated at block 312, for each Rechtschaffen and Kales event with a high probability. The same calculation is made at blocks 313 and 314 for each Rechtschaffen and Kales event with a medium and low probability, respectively. At this time, the relationship flags of k complex, spindle, and the occurrence of REM before or after an arousal in the epoch, are set at block 315, and the probabilities of the occurrence of Rechtschaffen and Kales events, based upon the Elemental Events, is calculated at blocks 316–325.

Figure 5C:
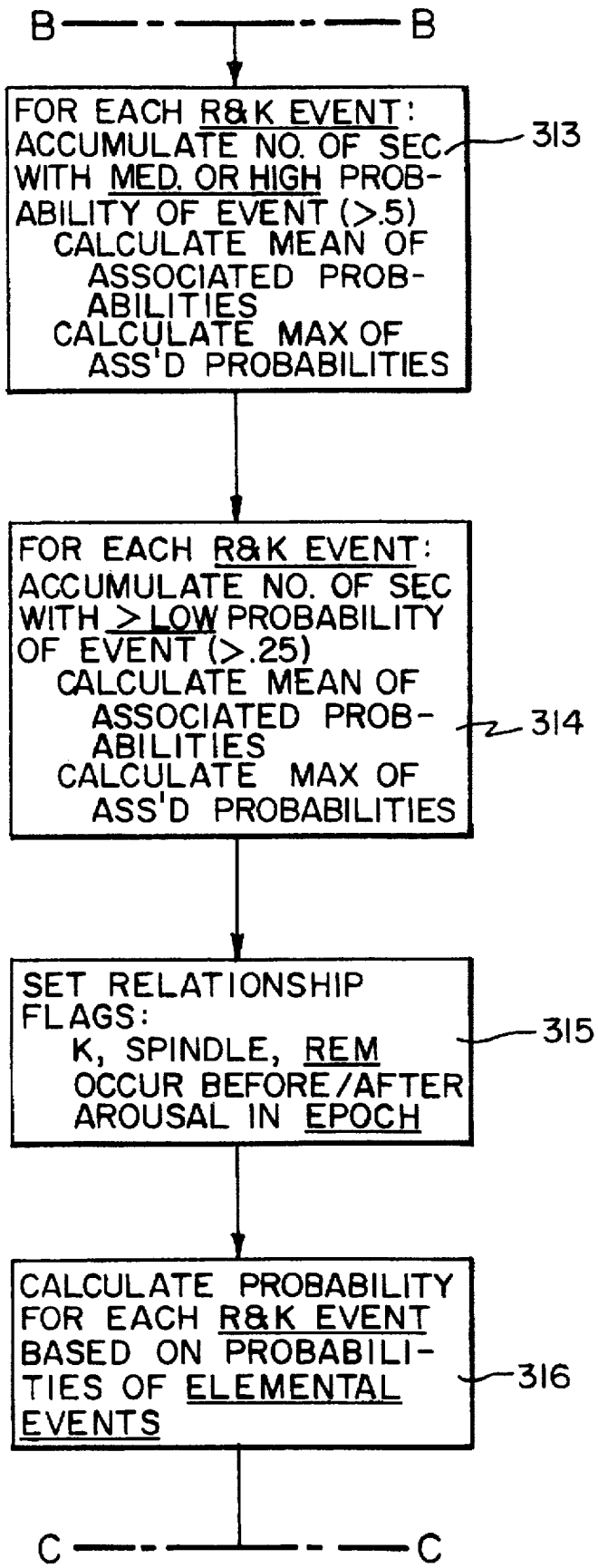
Figure 5D:
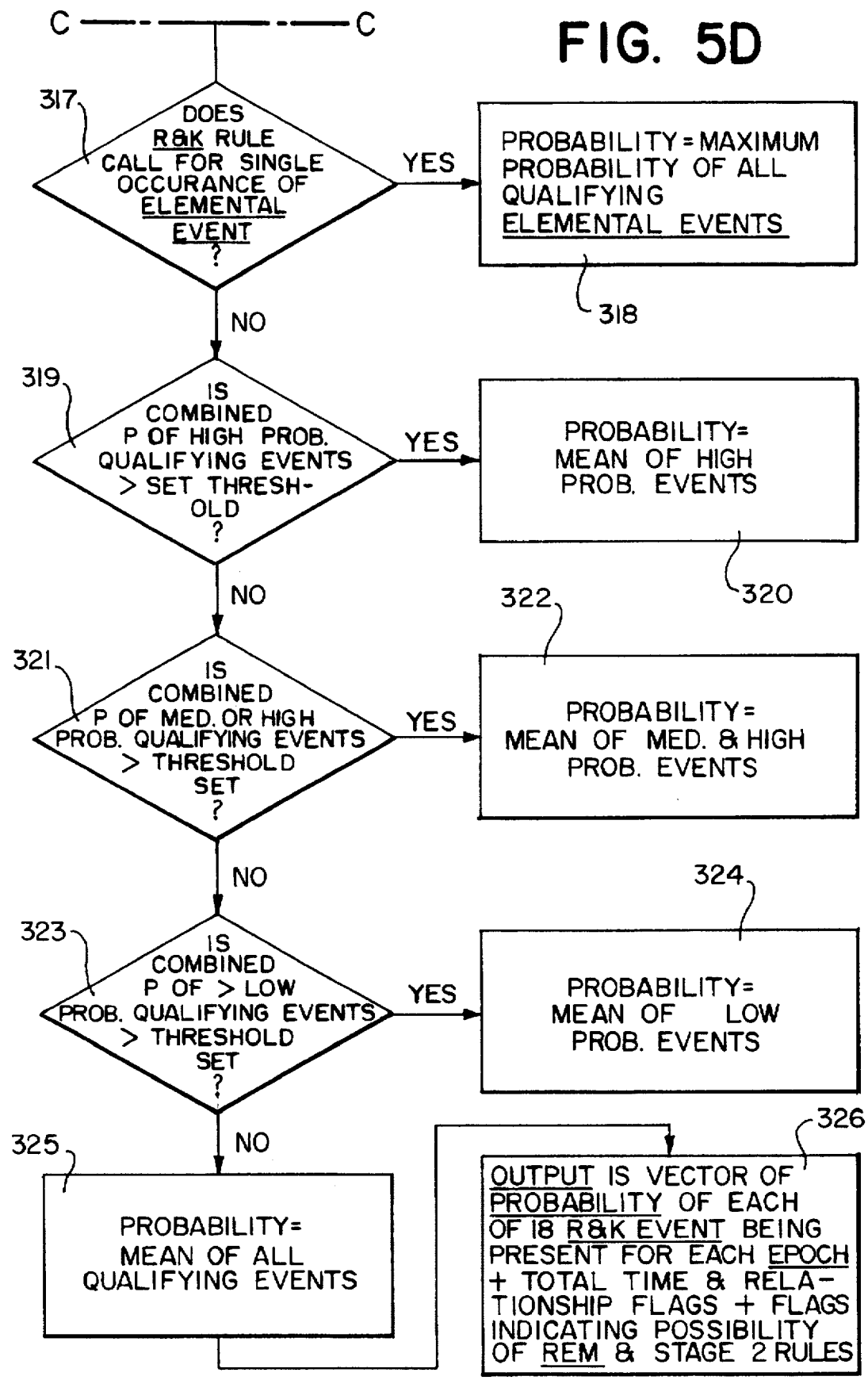

On the basis if this information, as shown in FIG. 5C, the various further probabilities are determined, in decision blocks 317, 319, 321 and 323, and output at blocks 318, 320, 322 and 324. The mean of all qualifying events is determined at block 325, and the resultant vectors are output at block 316.

Figure 6A:
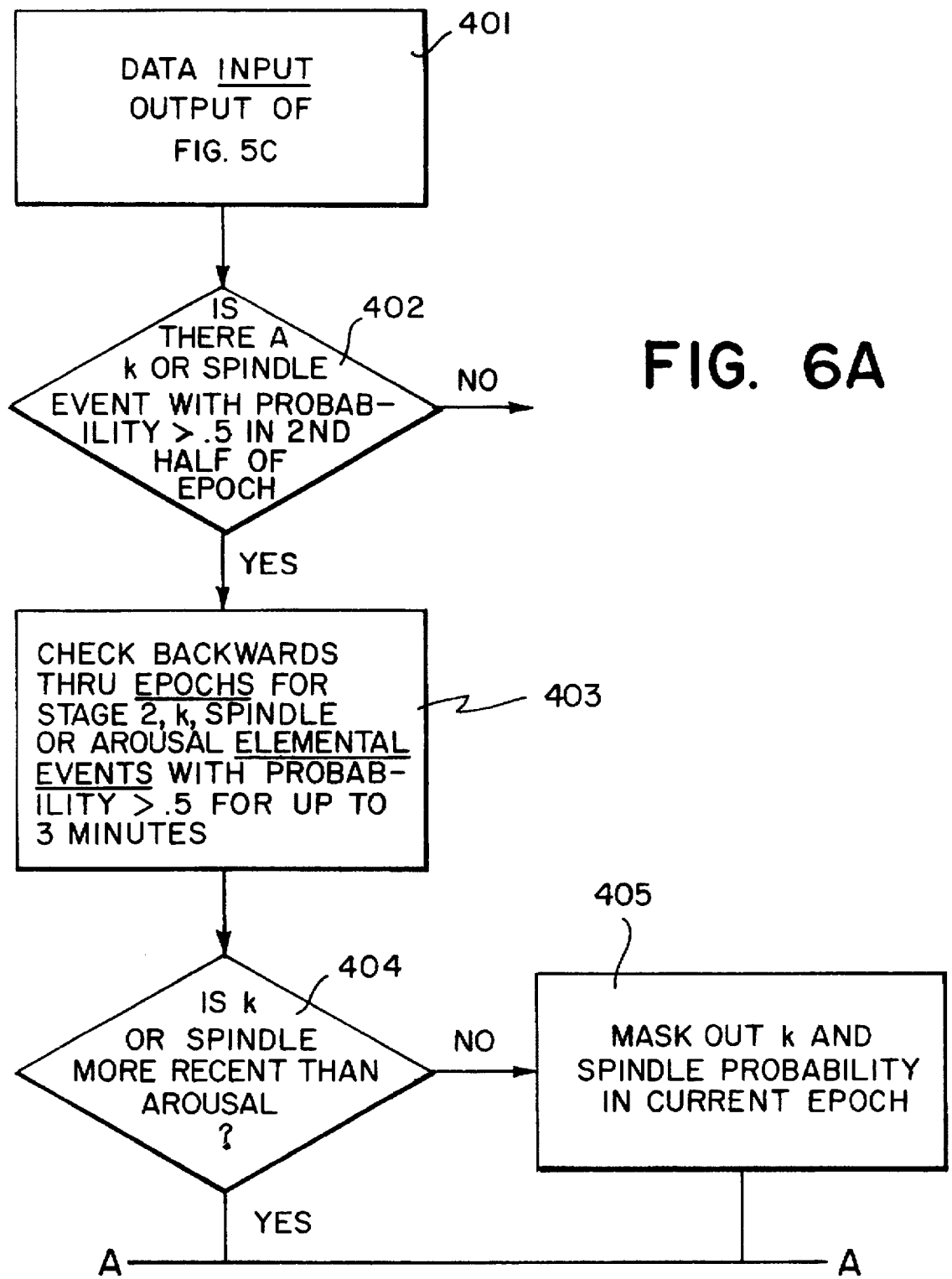
FIGS. 6A, 6B and 6C together constitute a flow diagram of a routine for modifying the probability matrix of Rechtschaffen and Kales events for the Stage 2 rule.

Following the assignment of probabilities of an Rechtschaffen and Kales event, in block 300, the determined probabilities are modified, in block 400, for the stage 2 rule. This rule requires that one consider other areas of the record for the presence of Elemental Events associated with Stage 2 but only if such consideration does not require the crossing of an arousal. An example of a routine for such modification is illustrated in FIGS. 6A. As illustrated, the data from FIG. 5C is input at block 401, and a determination is made at block 402 if a k complex or spindle has occurred with a probability of more than 0.5, in the second half of the epoch. If so, a backward check is made, at block 403, for stage 2, k complex, spindle events and arousals, with a probability of more than 0.5, for a period of 3 minutes. If such a k complex or spindle event has occurred more recently than an arousal, the 18 element vector is multiplied by an Rechtschaffen and Kales weighting matrix, at block 406. Otherwise, the k complex and spindle events are masked out, at block 405.

Figure 6B:
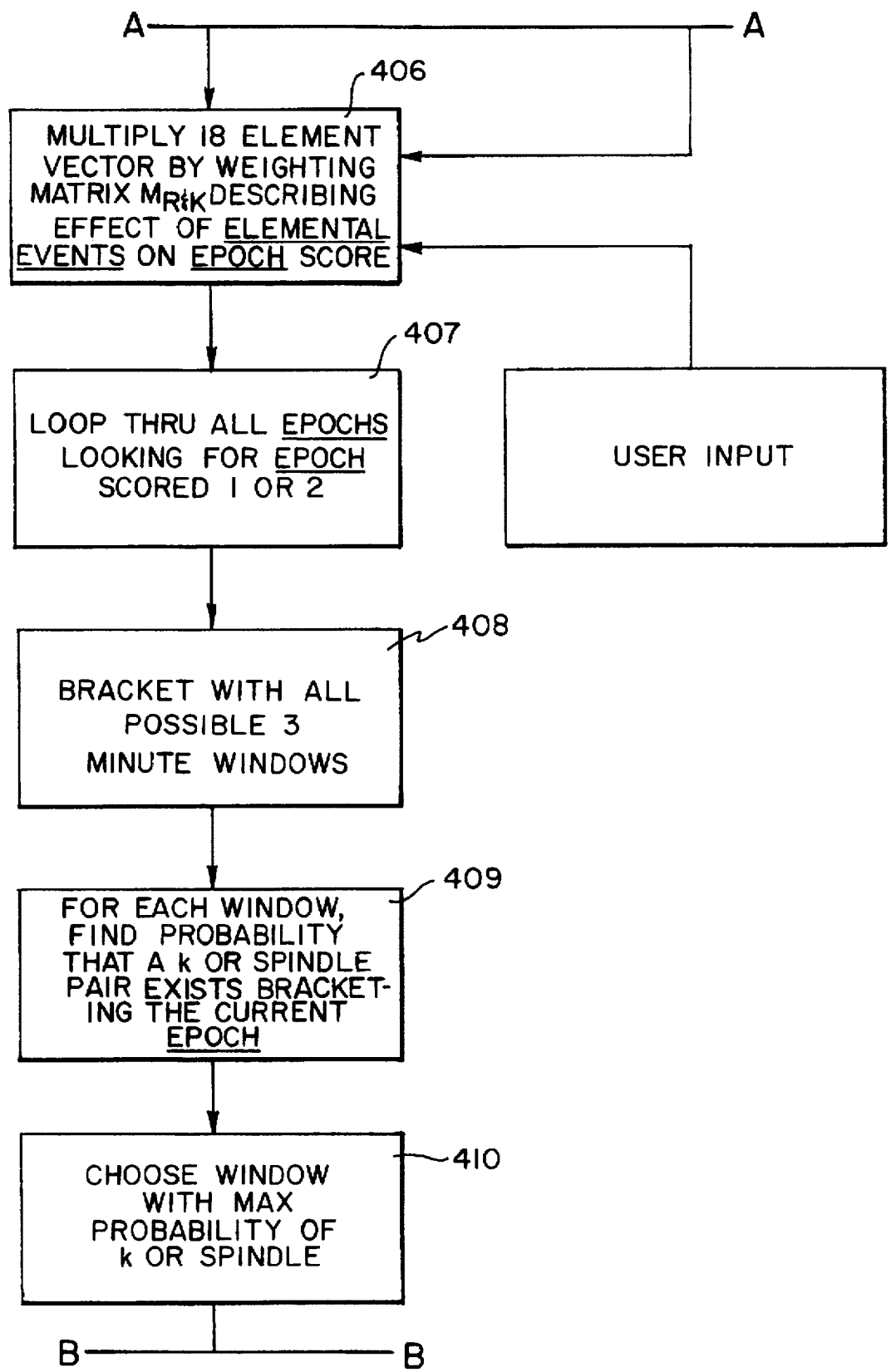

At this point, in block 406, the Rechtschaffen and Kales event vector is multiplied by a weighting matrix to produce a vector describing the initial sleep stage probability distribution. Now the program loops through all of the epochs, looking for an epoch scored 1 or 2, at block 407, and these are bracketed with all possible 3 minute windows, at block 408. The probability is now determined, at block 409, for each window, that a k complex or spindle pair exists within the brackets the current window surrouding the current epoch. As illustrated in FIG. 6B, a window is now chosen with a maximum probability of a k complex or spindle event, at block 410. If there is a probability more than 0.5 of a k complex or spindle, as detected at block 411, then this probability is temporarily moved into the present epoch. In either event, the 18 element vector is now multiplied by the weighting matrix, at block 412, and the resultant updated probabilities are output, at block 413.

Figure 6C:
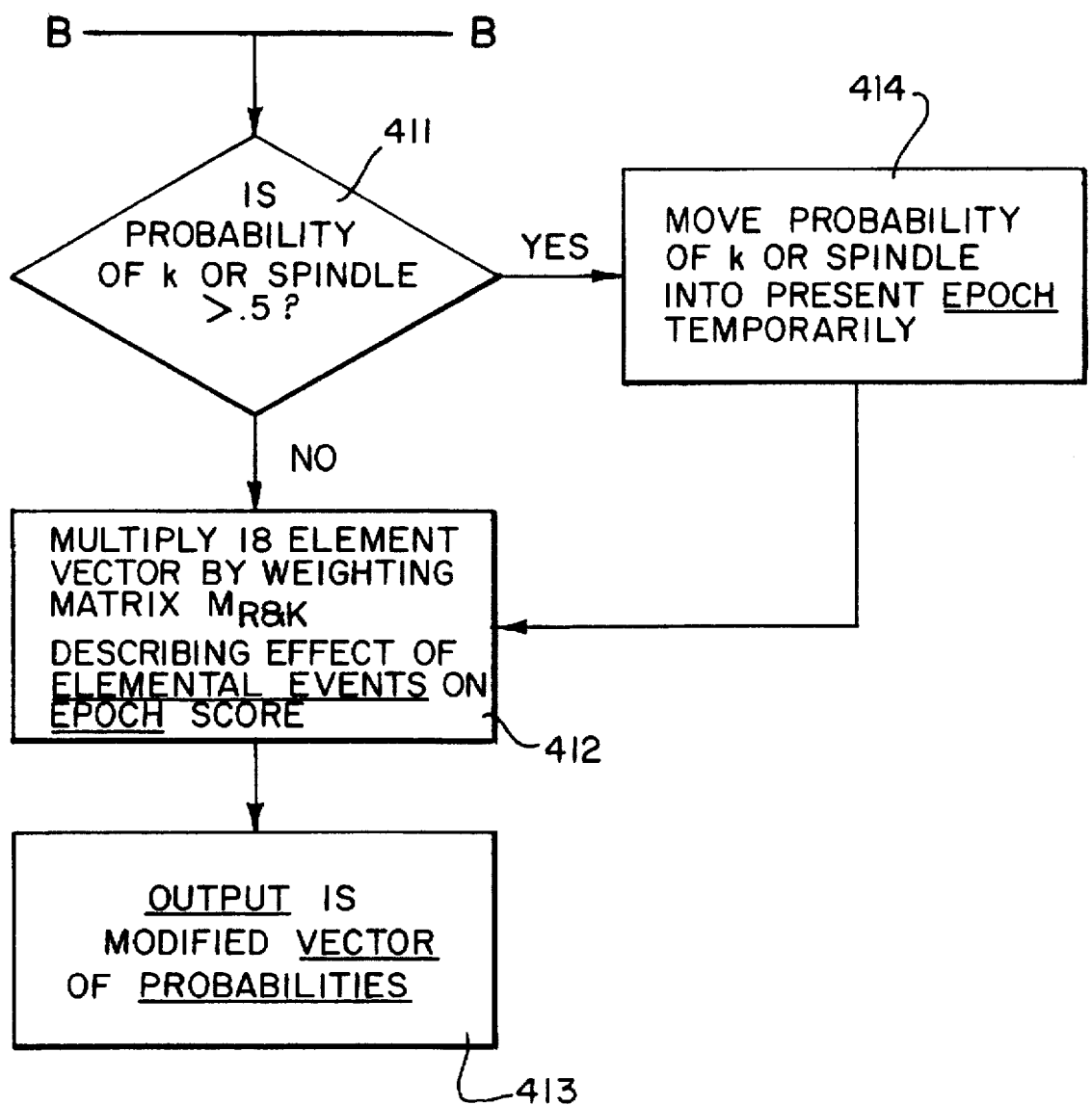
Figure 7A:
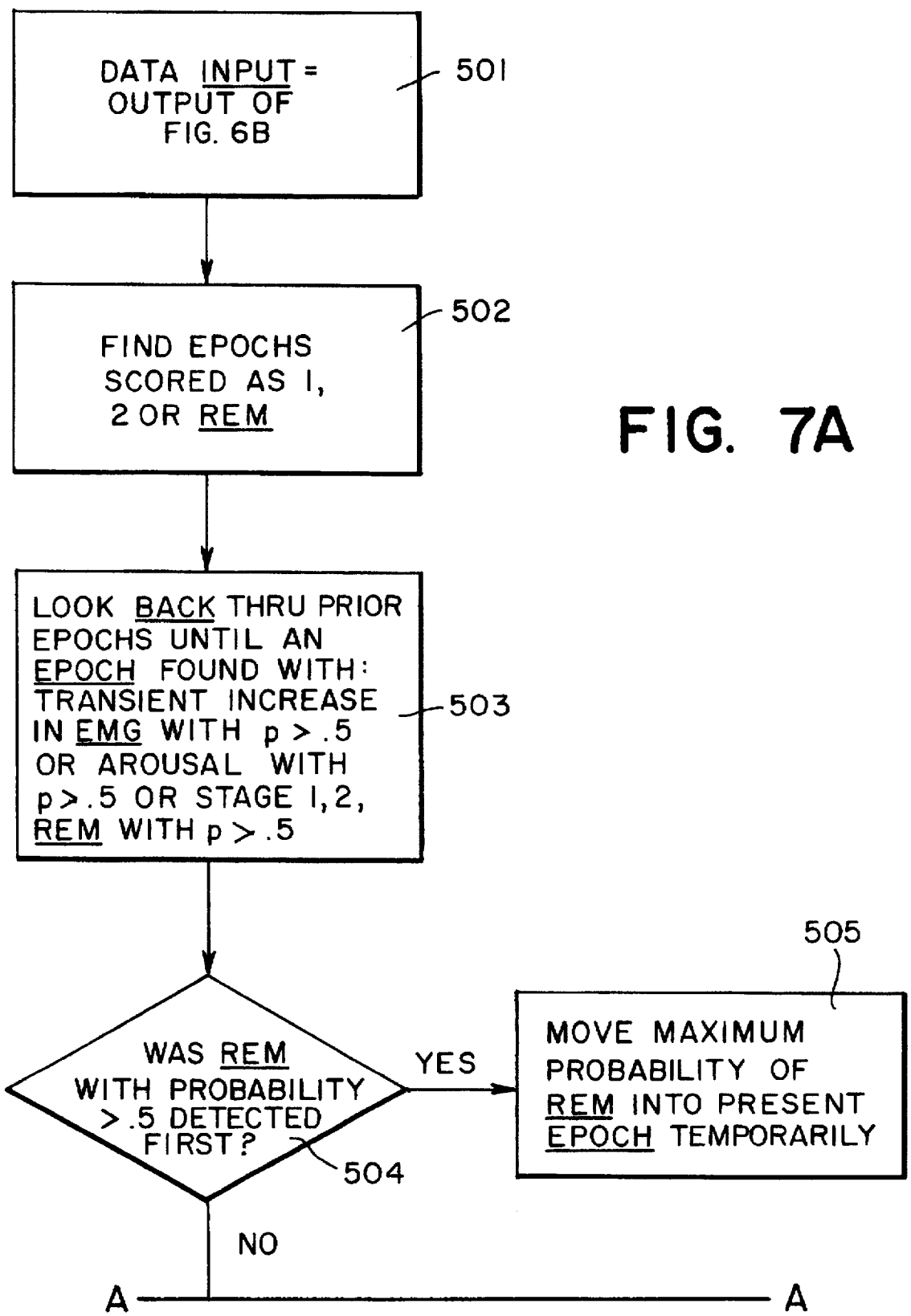
FIG. 7 is a flow diagram of a routine for modifying the probability matrix for Rechtschaffen and Kales events to account for the REM rule.
Figure 7B:
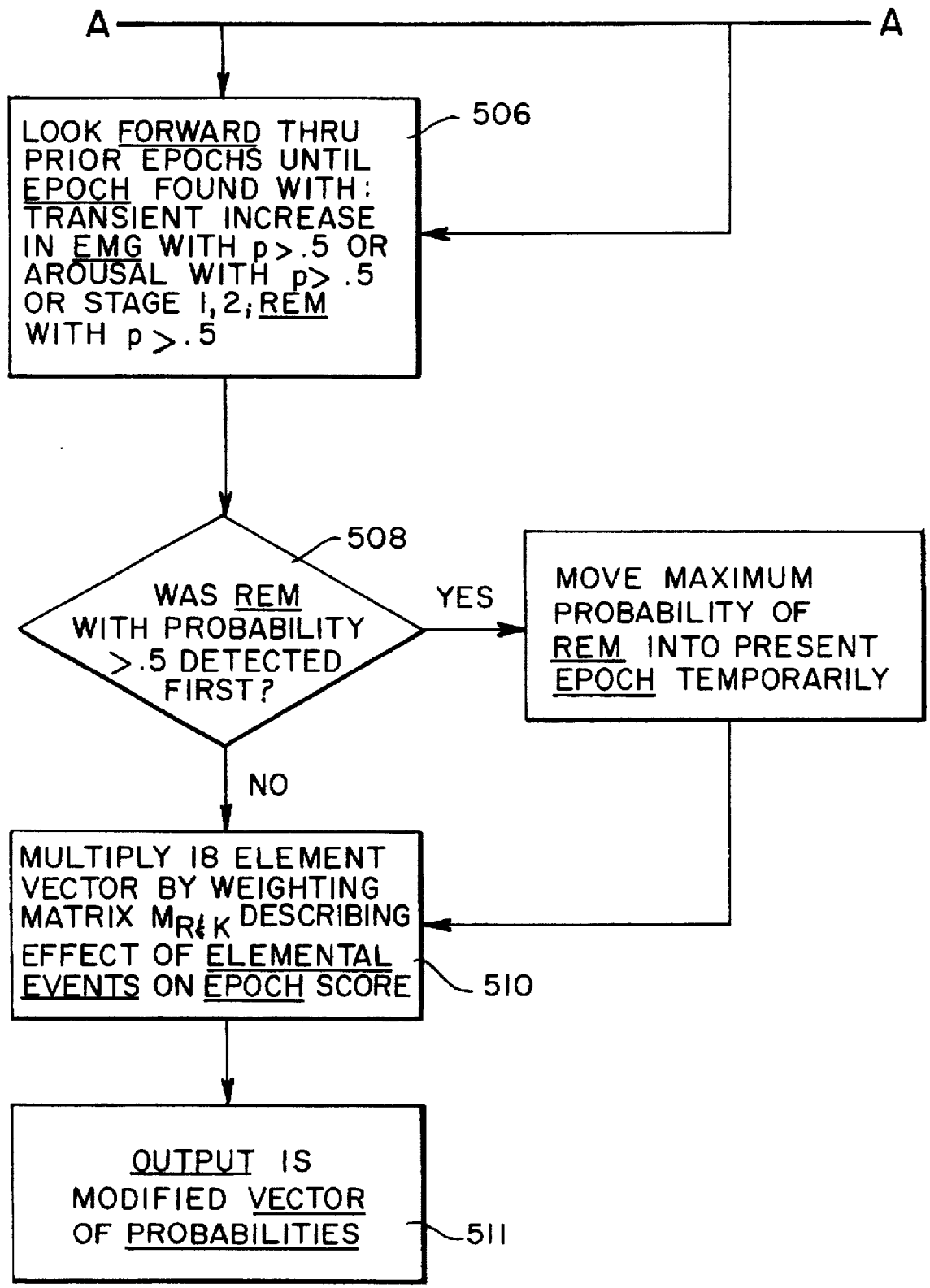

The probabilities modified by the routine of block 400, at block 500, are now modified for the REM rule. This rule states that, since rapid eye movements do not occur continuously during stage REM, an analysis must be made in prior and subsequent epochs in order to properly judge the probability of REM. An example of a routine for REM modification is illustrated in FIG. 7, wherein the data from the routine of FIG. 6 is input at block 501. The legends in the remainder of the blocks 502–511 in FIG. 7 is sufficiently descriptive that a detailed analysis is not necessary here.

Figure 8:
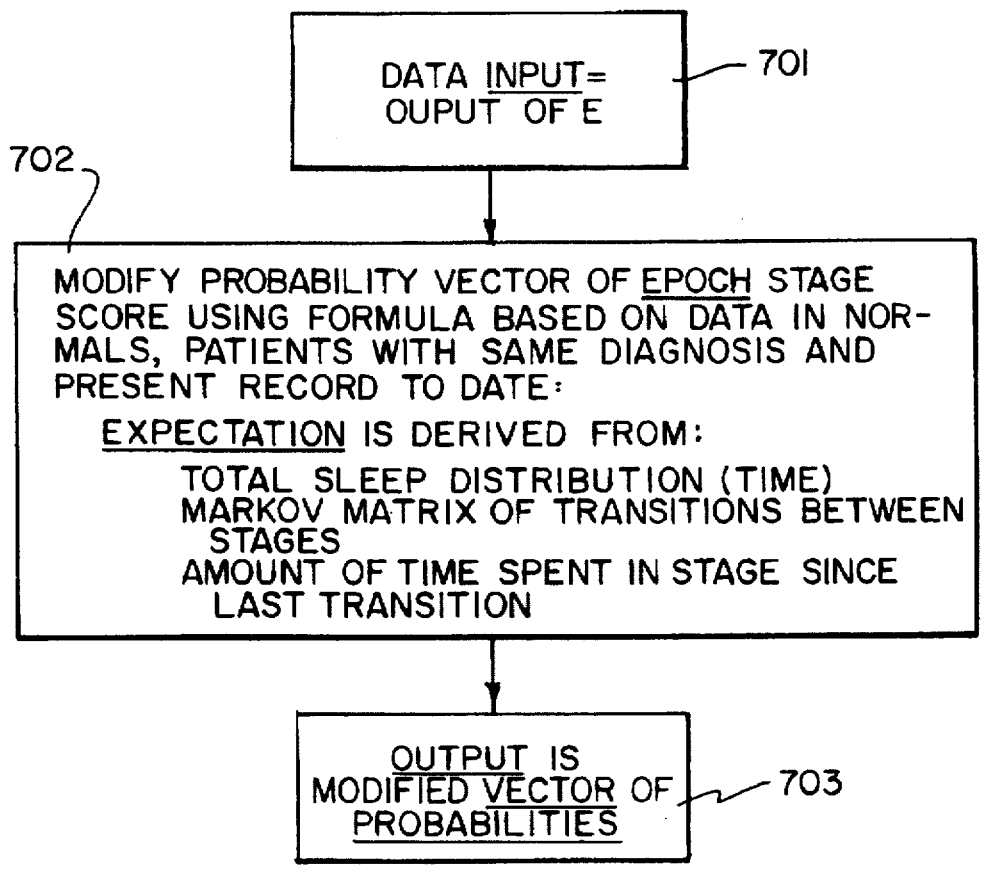
FIG. 8 is a flow diagram of a routine for applying a prior probability function.

The probabilities of the presence of each sleep stage (NREM 1–4 and REM) in each epoch is now calculated using an Rechtschaffen and Kales Event matrix and weighting factors, at block 600, and the probabilities resulting from the routine of block 600 are now modified on the basis of prior probability functions, at block 700. As described above, this routine modifies the score on the basis of data that is not present in the input signals. It may be derived, for example, from expected conditions of sleep, the expectation of transitions from one stage to another, and the during of time spent in a sleep stage before the transition occurs to another stage. An example of this step is illustrated in FIG. 8, wherein the data is input at block 701, modified at block 702 and output at block 703.

A loss function is now applied to the probabilities determined in block 700, at block 800. As defined above, the loss function is provided to assign a negative value to each possible error in assigning a sleep stage to an epoch, when it has been found that human scorers assign different sleeps stages to the epochs. An example of this modification is illustrated in FIG. 9, wherein the data is input at block 901, modified at block 902 and output at block 903.

The routine at block 900, in FIG. 2, may now be employed to provide an output indicating the sleep stages that the compute has determined to have the highest probabilities, and hence the least loss for error, in each epoch.

Figure 10:
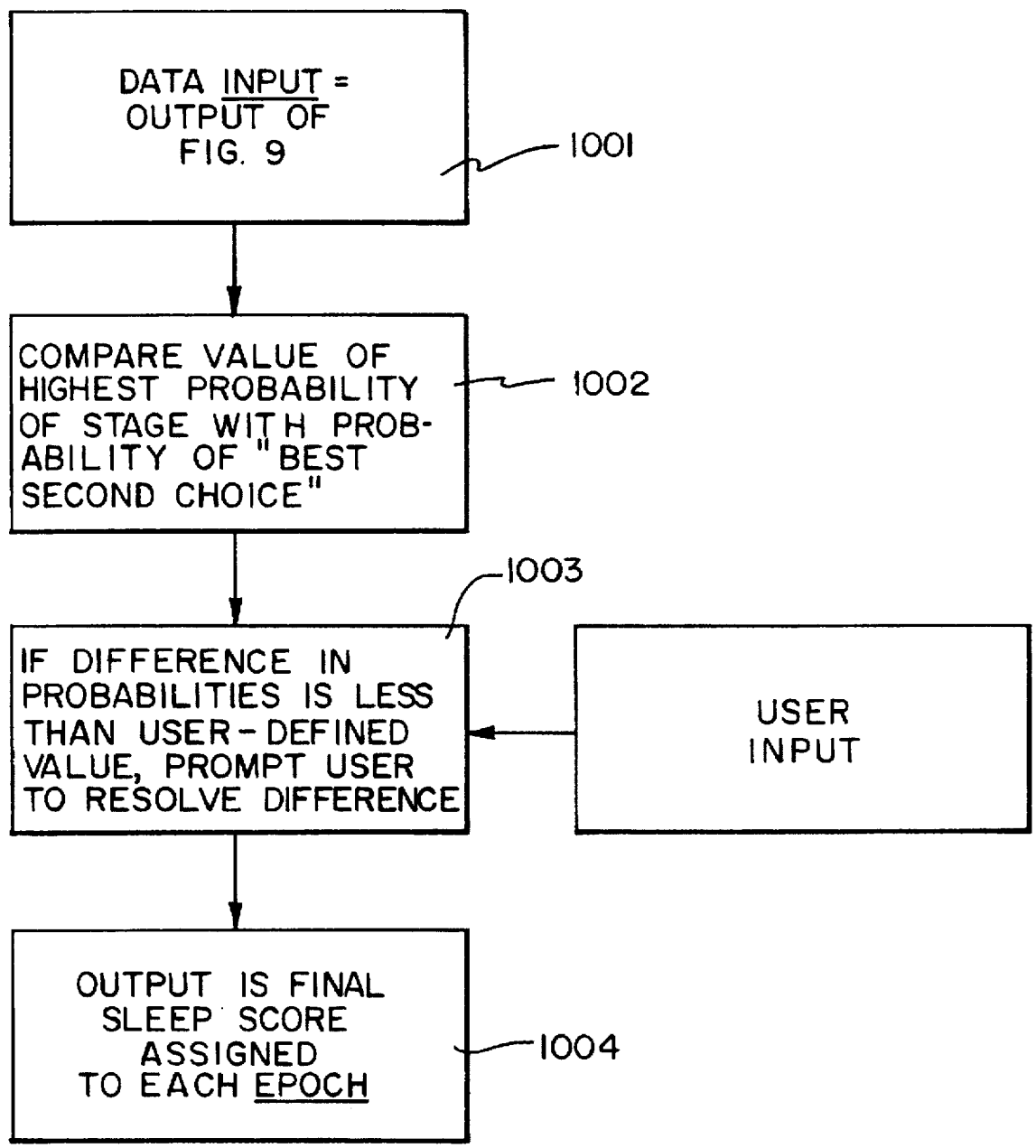
FIG. 10 is a flow diagram of a routine for resolving near-ties.

At this time, the program may resolve near-ties in the computer output, in the probabilities of existence of the different sleep stages, or exhibit such near-ties for the User of the program to resolve, at block 1000. An example of this routine is illustrated in FIG. 10, wherein the output of FIG. 9 is input at block 1001, and the values with the highest scores are compared with the second best scores at block 1002. If the difference is less than a predetermined amount, the human scorer must resolve the difference, at block 1003. An output at block 1004 constitutes a final sleep score assigned to each epoch.

Figure 12:
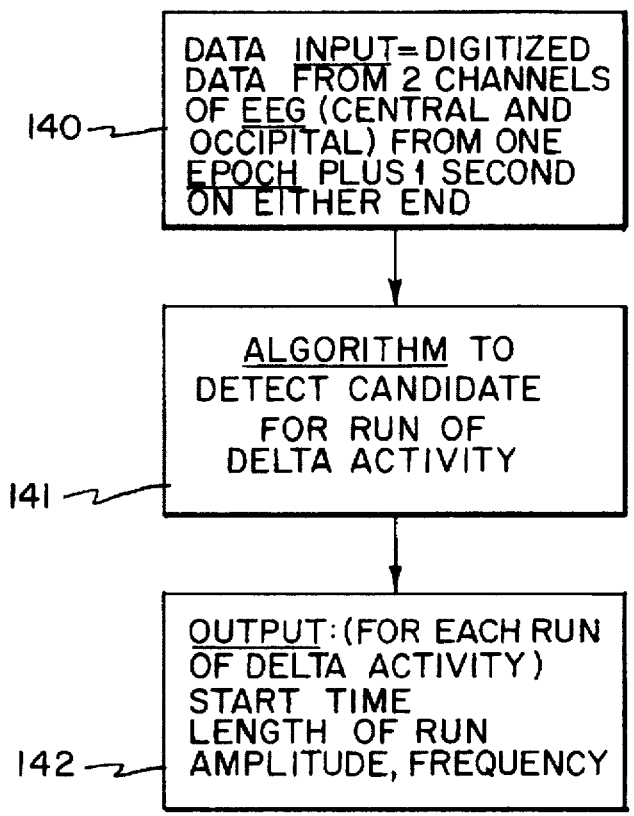
FIG. 12 is a flow diagram of a routine for detecting delta events.
Figure 13:
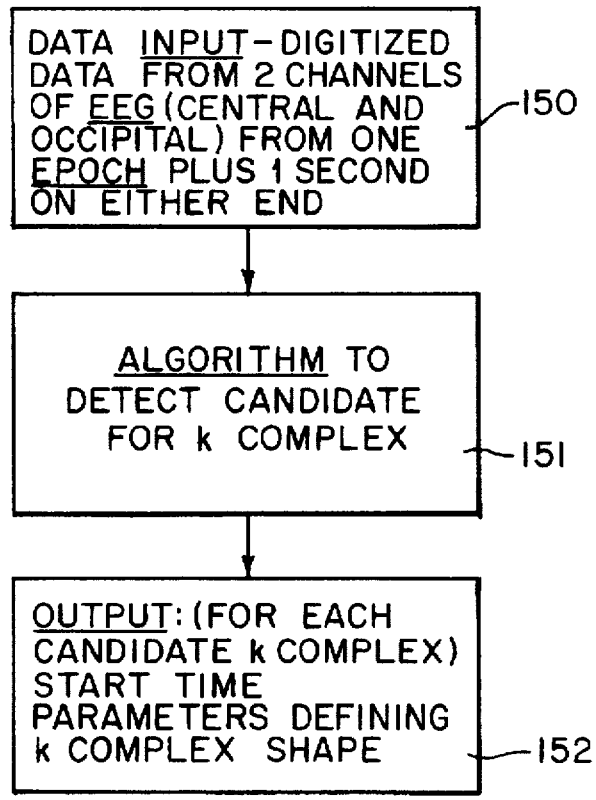
FIG. 13 is a flow diagram of a routine for detecting k complex events.
Figure 14:
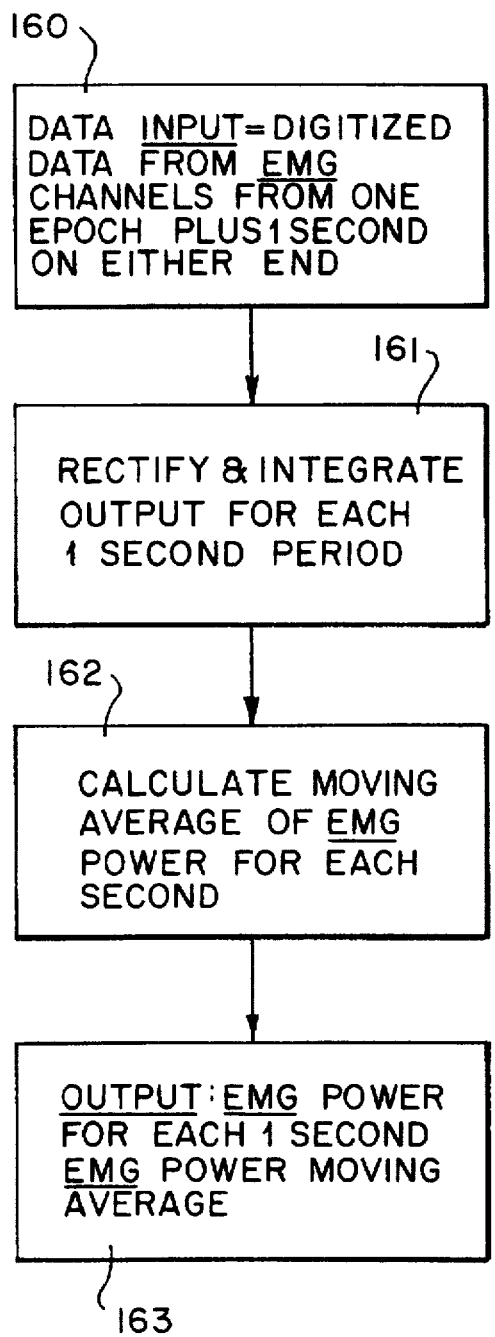
FIG. 14 is a flow diagram of a routine for detecting low, very low, high and transient increases in EMG events.

FIGS. 11–15 are simplified flow diagrams of routines for detecting the other Elemental Events. Thus, in FIG. 11, for the detection of sleep spindles, the data is input at block 130, subject to a suitable algorithm for the detection of the sleep spindle at block 131, and signals corresponding to the detected sleep spindles are output at block 132. This detector may be quite similar to that employed for detecting alpha waves, since the event is a short burst of activity in the 12 to 14 Hz band, that lasts from a half second to about one and a half seconds. It may occur only once during an epoch, once in every four epochs, etc., or it may not occur for hours. The spindle detector thus filters a different frequency band than the alpha detector, and detects somewhat different parameters. In the delta detection routine of FIG. 12, the input signals are input at block 140, subject to a suitable algorithm for delta wave detection at block 141, and the result of the detection is output at block 142. Similar routines are provided for detecting k complex events (FIG. 13), wherein the signals are input at block 150, subject to a suitable algorithm at block 151, and output at block 152. A common routine is provided to detect the events related to the various conditions and changes in EMG, as illustrated in FIG. 14, wherein the EMG signals are input at block 160, rectified and integrated for one second periods at block 161, with the moving average thereof being calculated at block 162. At block 163, signals are output corresponding to the EMG power for one second, and EMG power for the moving average.

Figure 15:
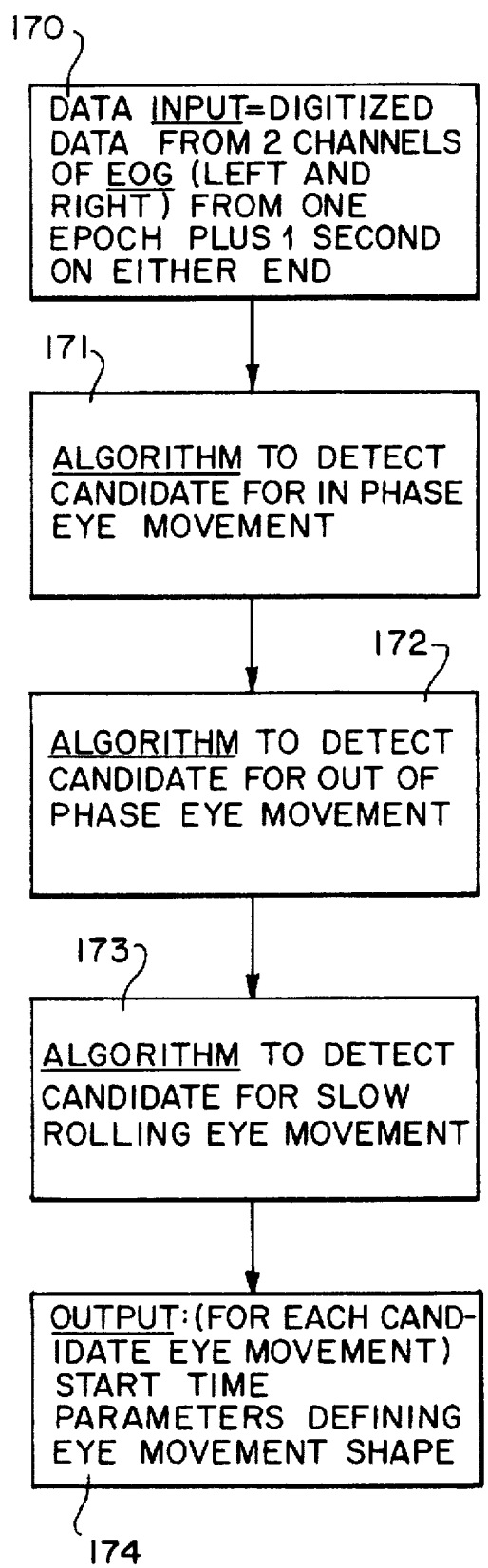
FIG. 15 is a flow diagram of a routine for detecting in-phase, out-of-phase and slow rolling eye movements.

The events related to eye movement may be detected in a common routine, as illustrated in FIG. 15. Thus, the EOG signals are received at block 170, the in-phase and out-of-phase eye movements and slow rolling eye movements are detected at blocks 171, 172 and 173, respectively, and the resultant signals are output at block 174.

Figure 18:
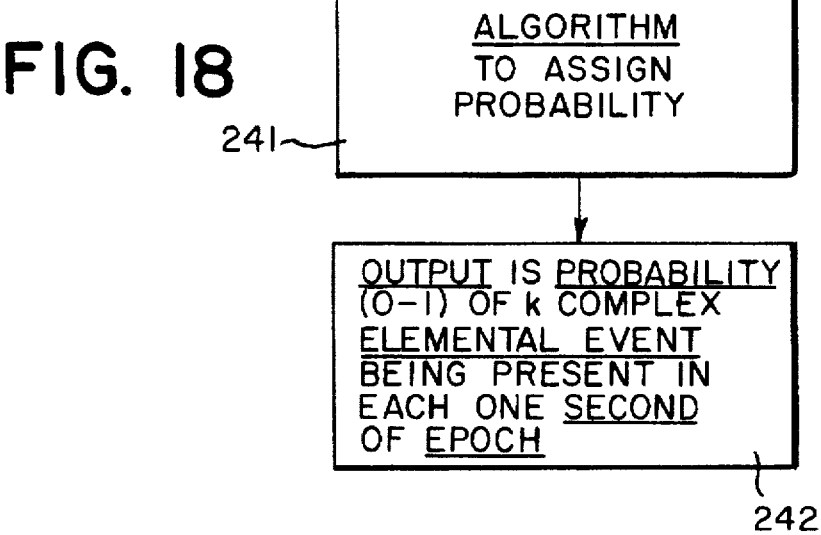
FIG. 18 is a flow diagram of a routine for assigning the probability of a k complex event.

FIGS. 16–20 are simplified flow diagrams of routines for assigning the probabilities of the presence of the other Elemental Events. Thus, FIG. 16 illustrates the input of signals, at block 220, from the routine of FIG. 11, for subjection to a suitable algorithm for assigning a probability to the presence of sleep spindles. This probability is output, at block 222, for each second of each epoch. A similar routine is provided for assigning the probability of the existence of delta events, in FIG. 17, wherein the signals output from the routine of FIG. 12 are input at block 17, subjected to a suitable algorithm at block 231, with the probability being output at block 232. In a similar manner, in order to assign the probability of the presence of k complex events, as shown in FIG. 18, the signals output from the routine of FIG. 13 are input at block 240, subjected to a suitable probability algorithm at block 241, with the probability being output at block 242.

Figure 19A:
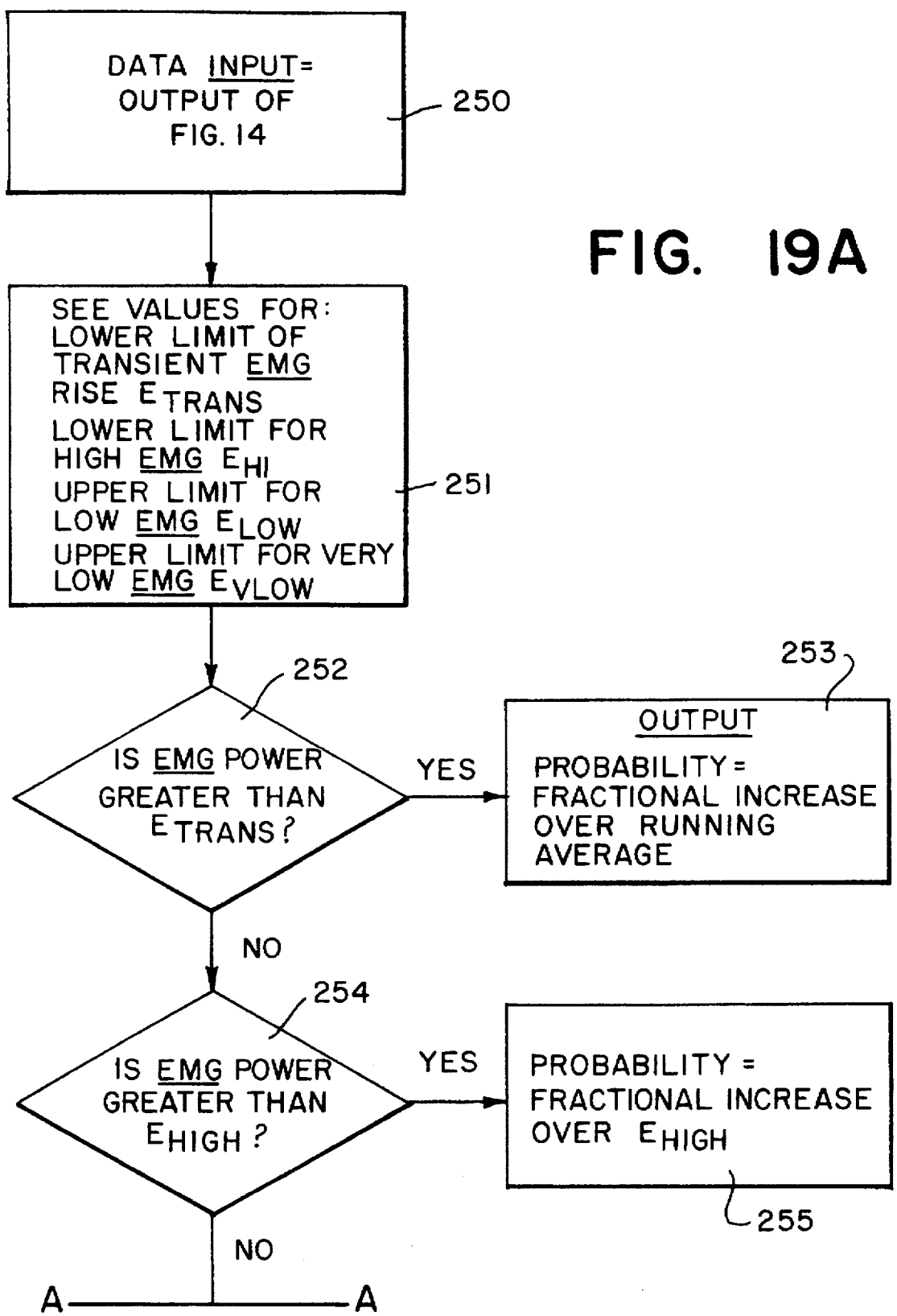
FIG. 19 is a flow diagram of a routine for assigning the probability of low, very low, high and transient EMG events.
Figure 19B:
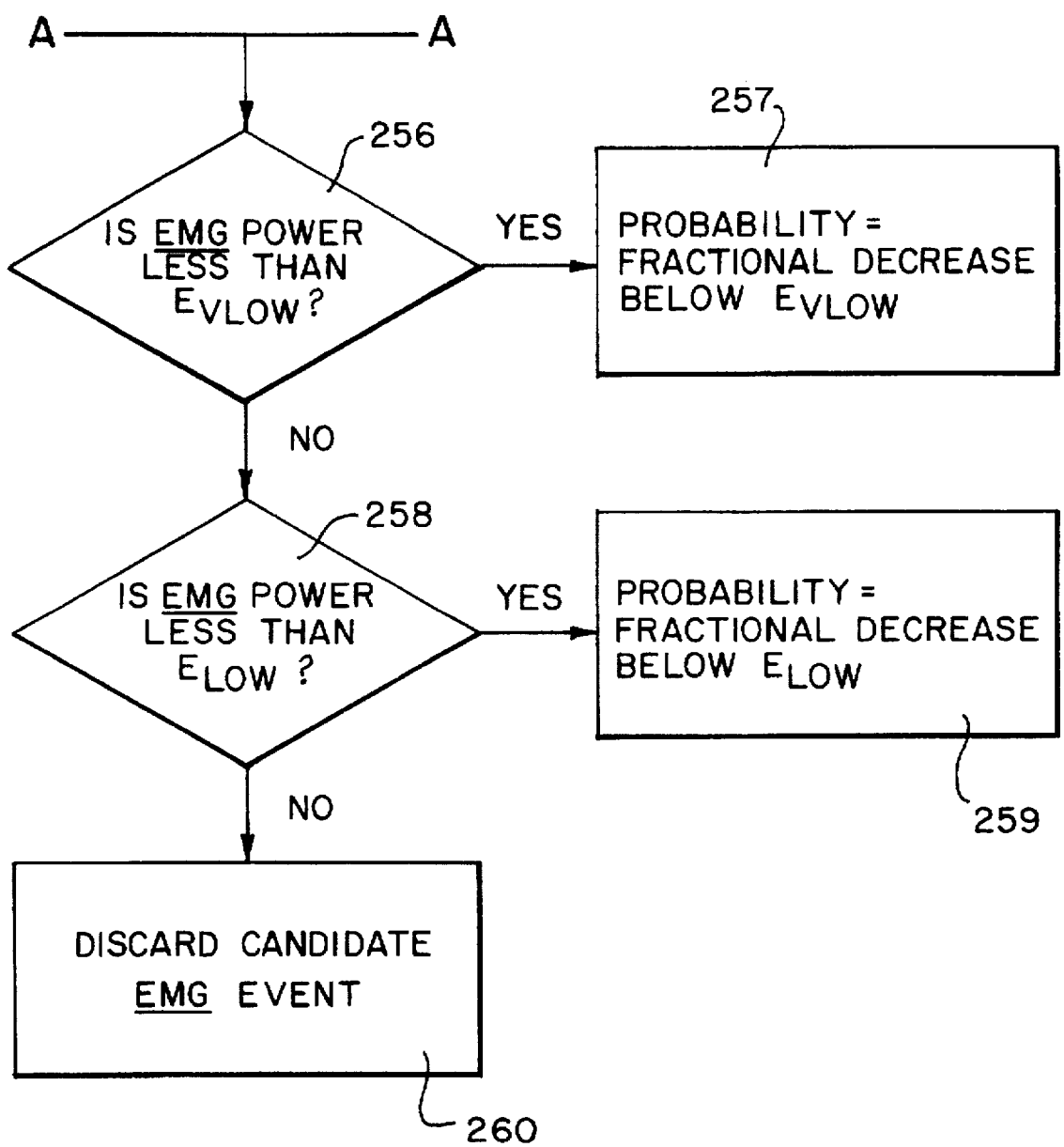

As shown at FIG. 19, the Events related to EMG signals may be subjected to a common routine, wherein the signals output from the routine of FIG. 14 are input at block 250. The parameters for distinguishing these events are set in block 251, and the existence of the various EMG power states are determined in the decision blocks 252, 254, 256 and 258. The probabilities of the existence of these states are output at the blocks 253, 255, 257 and 259, respectively, with the remaining candidates being discarded at block 260.

Figure 20:
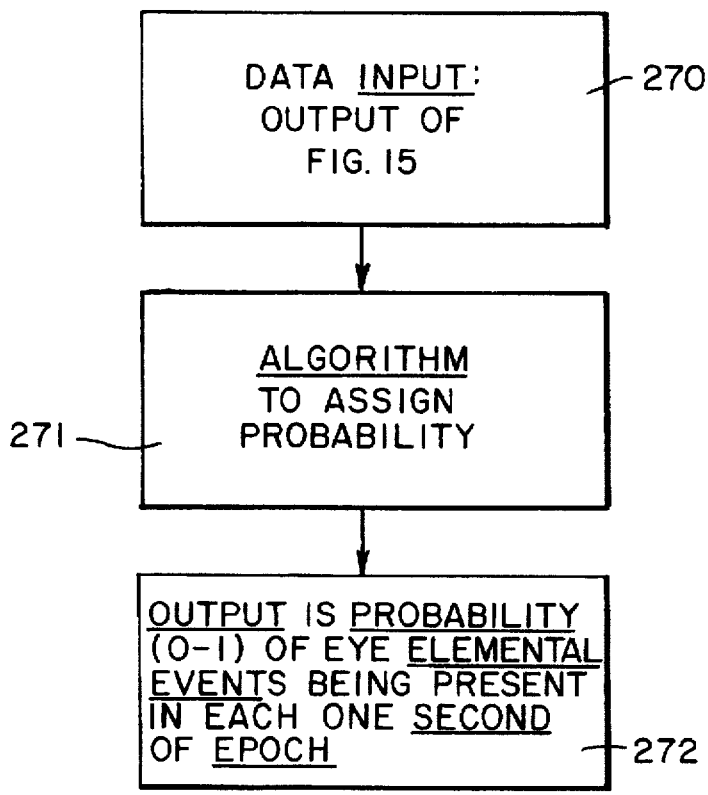
FIG. 20 is a flow diagram of a routine for assigning the probability of in-phase, out-of-phase and slow rolling eye movements.

The probability of the occurrence of the eye movement Events may be assigned in a common routine, as illustrated in FIG. 20, wherein the output of the routine of FIG. 15 is input at block 270, and subject to an assignment of probability of the existence of the various eye movement Events, at block 271. The assigned probabilities are output at block 272.

The Appendix at the end of this specification is a program, written in C, for the practice of the invention. The various routines, as discussed above, are indicated by the comments in this listing.

While the invention has been disclosed and described with reference to a limited number of examples, it will be apparent that variations and modifications may be made therein, and it is accordingly intended in the following claims to cover each such variation and modification that falls within the true spirit and scope of the invention.

What is claimed is:

1. A method for computer analysis of polysomnograph waveforms to score epochs of such polysomnograph waveforms, said score constituting one of a plurality of sleep stages using standard Rechtschaffen and Kales (R&K) sleep stage scoring rules, comprising the steps:

(a) computer separating said polysomnograph signals into a plurality of sequential epochs, each epoch possibly having associated with it elemental events which can be used to associate with R&K events, said R&K events being usable to determine a score for each of the epochs, said elemental events comprising a member selected from the group consisting of:

A1: run of alpha (α) waves
A2: sleep spindle
A3: delta (δ) wave
A4: K complex
A5: low EMG
A6: very low EMG
A7: high EMG
A8: transient increase in EMG
A9: in-phase eye movement
A10: out-of-phase eye movement
A11: slow rolling eye movement, said R&K events comprising a member selected from the group consisting of:

C1: alpha (α) waves <25% of epoch
C2: alpha waves in 25–50% of epoch
C3: alpha waves in >50% of epoch
C4: single sleep spindle in epoch
C5: multiple sleep spindles in epoch
C6: delta (δ) waves in <20% of epoch
C7: delta waves in 20–50% of epoch
C8: delta waves in >50% of epoch
C9: k complexes in epoch
C10: low EMG for most of epoch
C11: very low EMG for most of epoch
C12: high EMG for most of epoch
C13: transient increase in EMG during epoch
C14: in-phase eye movements C15: out-of-phase eye movements (REMS)
C16: slow rolling eye movements
C17: 5 second arousal
C18: significant artifacts, (b) computer determining whether there is a possibility of the existence of each of the elemental events in the polysomnograph waveforms of each of said epochs, the elemental events which have been determined to be possibly present constituting elemental event candidates having a certain probability of being present, (c) then computer determining the probabilities of the existence of each of said elemental event candidates in each epoch of the polysomnograph waveforms, (d) then, computer employing said probabilities determined in step (c), computer producing first signals representing the probability of an R&K event in each epoch of the polysomnograph waveforms, (e) then, computer producing from the first signals a second signal representing a probability distribution of sleep stages based on said probability of an R&K event, said second signal determining the score constituting a standard R&K sleep stage, wherein said standard R&K sleep stage is selected from the group consisting of:

Non-REM (NREM) Stage 1
Non-REM (NREM) Stage 2
Non-REM (NREM) Stage 3
Non-REM (UREM) Stage 4
Rapid Eye Movement (REM) Stage
Awake
Movement Time
Artifact, (f) outputting the score determined in step (e).

2. The method of claim 1, further comprising probabilistically modifying said first signals using a stage 2 rule to produce modified first signals, said stage 2 rule comprising analyzing polysomnograph signals of other epochs for the presence of elemental events associated with Non-REM (NREM) Stage 2, and using the Non-REM (NREM) Stage 2 associated elemental events in the other epochs to increase or decrease said first signals in accordance with whether the Non-REM (NREM) Stage 2 elemental events are present or absent, respectively, in said other epochs.

3. The method of claim 2, wherein the polysomnograph waveforms in said other epochs may represent an arousal when the patient which is the source of the polysomnograph waveforms may temporarily awake, and when the arousal in said other epochs is detected, the non-REM (NREM) Stage 2 associated elemental events in said other epochs are ignored.

4. The method of claim 3, further comprising probabilistically modifying said modified first signals using a Rapid Eye Movement (REM) stage rule, said Rapid Eye Movement (REM) stage rule comprising analyzing polysomnograph waveforms of said other epochs for the presence of elemental events associated with Rapid Eye Movement (REM) stage, and using the Rapid Eye Movement (REM) stage associated elemental events in said other epochs to increase or decrease said modified first signals in accordance with whether the Rapid Eye Movement (REM) stage associated elemental events are present or absent, respectively, in said other epochs.

5. The method of claim 4, further comprising the displaying of the probabilities determined in step (c).

6. The method of claim 1, wherein the first signals produced by step (d) indicate close probabilities of different R&K events, further comprising displaying the polysomnograph waveforms and prompting a user to decide between the different R&K events with the close probabilities.

7. Apparatus for computer analysis of polysomnograph waveforms to score epochs of such polysomnograph waveforms, said score constituting one of a plurality of sleep stages using standard Rechtschaffen and Kales (R&K) sleep stage scoring rules, comprising:

(a) computer means for separating said polysomnograph signals into a plurality of sequential epochs, each epoch possibly having associated with it elemental events which can be used to associate with R&K events, said R&K events being usable to determine a score for each of the epochs, said elemental events comprising a member selected from the group consisting of:

A1: run of alpha ($\alpha$) waves
A2: sleep spindle
A3: delta ($\delta$) wave
A4: K complex
A5: low EMG
A6: very low EMG
A7: high EMG
A8: transient increase in EMG
A9: in-phase eye movement
A10: out-of-phase eye movement
A11: slow rolling eye movement, said R&K events comprising a member selected from the group consisting of:
C1: alpha ($\alpha$) waves <25% of epoch
C2: alpha waves in 25–50% of epoch
C3: alpha waves in >50% of epoch
C4: single sleep spindle in epoch
C5: multiple sleep spindles in epoch
C6: delta ($\delta$) waves in <20% of epoch
C7: delta waves in 20–50% of epoch
C8: delta waves in >50% of epoch
C9: k complexes in epoch
C10: low EMG for most of epoch
C11: very low EMG for most of epoch
C12: high EMG for most of epoch
C13: transient increase in EMG during epoch
C14: in-phase eye movements
C15: out-of-phase eye movements (REMS)
C16: slow rolling eye movements
C17: 5 second arousal
C18: significant artifacts.

(b) computer means for determining whether there is a possibility of the existence of each of the elemental events in the polysomnograph waveforms of each of said epochs, the elemental events which have been determined to be possibly present constituting elemental event candidates having a certain probability of being present, (c) computer means for determining the probabilities of the existence of each of said elemental event candidates in each of said epochs of the polysomnograph waveforms, (d) computer means for employing said probabilities determined in step (c) and for producing first signals representing the probability of an R&K event in each of said epochs of the polysomnograph waveforms, (e) computer means for producing from the first signals a second signal representing a probability distribution of sleep stages based on said probability of an R&K event, said second signal determining the score constituting a standard R&K sleep stage, wherein said standard R&K sleep stage is selected from the group consisting of:
Non-REM (NREM) Stage 1
Non-REM (NREM) Stage 2
Non-REM (NREM) Stage 3
Non-REM (NREM) Stage 4
Rapid Eye Movement (REM) Stage
Awake
Movement Time
Artifact.

* * * * *